United States Patent [19]

Boberg et al.

[11] 4,416,880
[45] Nov. 22, 1983

[54] β-LACTAM ANTIBIOTICS AND COMPOSITIONS CONTAINING THE SAME

[75] Inventors: Michael Boberg; Karl G. Metzger, both of Wuppertal, Fed. Rep. of Germany

[73] Assignee: Bayer Aktiengesellschaft, Leverkusen, Fed. Rep. of Germany

[21] Appl. No.: 304,280

[22] Filed: Sep. 21, 1981

[30] Foreign Application Priority Data

Oct. 8, 1980 [DE] Fed. Rep. of Germany ....... 3037997

[51] Int. Cl.³ .............. C07D 499/70; A61K 31/545; A61K 31/43; C07D 501/22; C07D 501/36
[52] U.S. Cl. ........................ 424/246; 260/239.1; 424/248.51; 424/271; 542/429; 542/430; 542/432; 542/436; 542/453; 542/455
[58] Field of Search ............... 260/239.1; 542/429, 542/430, 432, 436, 453, 455; 424/246, 248.51, 271, 270

[56] References Cited

U.S. PATENT DOCUMENTS

| | | | |
|---|---|---|---|
| 4,014,869 | 3/1977 | Gregory et al. | 424/246 X |
| 4,182,868 | 1/1980 | Ochiai et al. | 544/21 |
| 4,205,072 | 5/1980 | Vignau et al. | 424/246 |
| 4,275,062 | 6/1981 | Breuer et al. | 424/246 |
| 4,288,436 | 9/1981 | Takaya et al. | 424/246 |
| 4,298,606 | 11/1981 | Ochiai et al. | 424/246 |
| 4,310,459 | 1/1982 | Cundall et al. | 260/239.1 |

Primary Examiner—Natalie Trousof
Assistant Examiner—Vera C. Clarke

Attorney, Agent, or Firm—Sprung, Horn, Kramer & Woods

[57] ABSTRACT

β-Lactam antibiotics of the formula

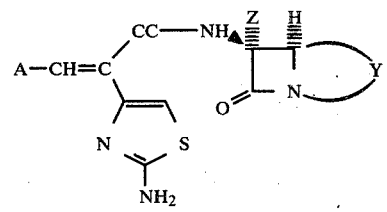

in which
A is a hydrogen atom, an optionally substituted alkyl, alkenyl, alkinyl or cycloalkyl group, a substituted or unsubstituted phenyl ring, a polycyclic aromatic ring or an optionally substituted heterocyclic 5-membered or 6-membered ring with 1 to 4 hetero-atoms,
Y is

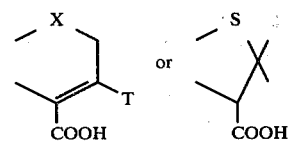

X is a sulphur or oxygen atom,
T is an organic radical, and
Z is a hydrogen atom or a $C_1$ to $C_6$ alkoxy group, or an ester or salt thereof.

8 Claims, No Drawings

β-LACTAM ANTIBIOTICS AND COMPOSITIONS CONTAINING THE SAME

The invention relates to certain new β-lactam compounds, to processes for their production and to agents, such as medicaments, in particular antibacterial agents, and also to agents for promoting growth and for improving feed utilization in animals, as well as to antioxidants.

β-Lactam compounds which carry a substituted acrylamido side chain have already been described.

Thus, for example, penicillin compounds which contain the structural element

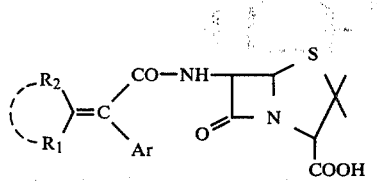

wherein

Ar is a substituted phenyl ring or a heterocyclic radical and $R^1$ and $R^2$ represent substituted or unsubstituted alkyl groups or a cycloalkyl group, are mentioned in Belgian Patent Specification No. 633,397 and in U.S. Pat. No. 3,622,569.

Furthermore, U.S. Pat. No. 4,014,869 describes cephalosporin compounds with an acrylamido side chain which is in the Z-configuration and carries, inter alia, aromatic or heterocyclic radicals in the 2-position and 3-position:

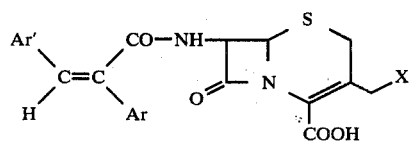

According to the present invention we provide compounds which are β-lactam compounds which correspond to the general formula

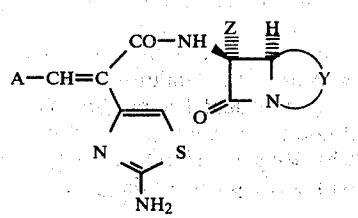

esters, or salts, including inner salts, thereof, wherein

A denotes a hydrogen atom, an optionally substituted alkyl, alkenyl, alkinyl or cycloalkyl group, a substituted or unsubstituted phenyl ring, a polycyclic aromatic ring or an optionally substituted heterocyclic 5-membered or 6-membered ring with 1 to 4 hetero-atoms, and wherein Y in the form of the free acid denotes a radical of the general formula

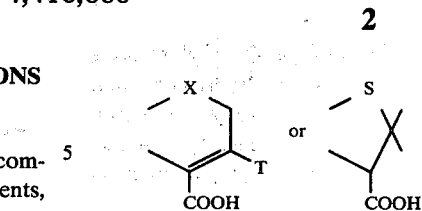

wherein

X denotes a sulphur or oxygen atom and

T is an organic radical, and wherein

Z denotes a hydrogen atom or a $C_1$ to $C_6$ alkoxy group.

The compounds according to the present invention have very good antibacterial properties.

If A represents an alkyl, alkenyl or alkinyl radical, it is preferably a straight-chain or branched, optionally substituted radical with up to 18 carbon atoms, particularly preferably with up to 12 carbon atoms and especially with up to 6 carbon atoms.

Substituents for alkyl, alkenyl, alkinyl and cycloalkyl radicals include, in the context of the present invention, double-bonded oxygen, nitrogen or sulphur.

The polycyclic aromatic ring in the definition of radical A includes, in the context of the present invention, such rings which contain hetero-atoms.

A preferably represents a phenyl radical of the general formula

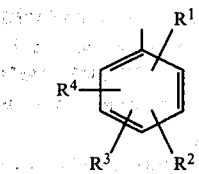

wherein $R^1$, $R^2$, $R^3$ and $R^4$ independently of one another denote a hydrogen or halogen atom, an optionally substituted alkyl, alkenyl, alkinyl or cycloalkyl group with up to 6 carbon atoms, an aryl radical, a $-OCOR^5$ group,

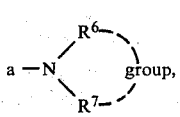

or a hydroxyl, trifluoromethyl, nitro, cyano, $C_1$ to $C_6$ alkoxy, $C_1$ to $C_6$ alkylthio, hydroxycarbonyl, ($C_1$ to $C_6$ alkoxy)-carbonyl, aminocarbonyloxy, sulphonyl or sulpho group, wherein the aryl radical in turn denotes a substituted or unsubstituted carbocyclic aromatic ring or 5-membered or 6-membered heterocyclic ring, and wherein $R^5$ denotes a branched or unbranched optionally substituted alkyl, alkenyl or alkinyl group with up to 6 carbon atoms or an optionally substituted cycloalkyl group, and wherein $R^6$ and $R^7$ independently of one another are a hydrogen atom, or together or independently of one another denote an optionally substituted alkyl, alkenyl, alkinyl or cycloalkyl group or a $C_1$ to $C_6$ alkanoyl group.

With regard to the definition of Y, preferred compounds are those in which

X denotes a sulphur or oxygen atom and

T denotes a hydrogen atom, a $C_1$ to $C_4$ alkyl group, a halogen atom or a $C_1$ to $C_4$ alkoxy, hydroxymethyl, formyloxymethyl, ($C_1$ to $C_4$ alkyl)-carbonyloxymethyl, aminocarbonyloxymethyl, pyridiniummethyl, 4-carbamoylpyridiniummethyl or heterocyclylthiomethyl group, wherein "heterocyclyl" preferably represents a radical of the general formula wherein $R^8$ denotes a hydrogen atom or a methyl, 2-dimethylaminoethyl, carboxymethyl, or sulphomethyl group and $R^9$ denotes a hydrogen atom or a methyl group.

In the compounds of formula (I) of the present invention, for each structural formula there exists a compound with the E-configuration and a compound with the Z-configuration according to the E/Z nomenclature described in J. Amer. Chem. Soc. 90, 509 (1968). Compounds which are preferred according to the invention are those with the Z-configuration.

The compounds of the present invention can be in the form of free acids, of esters, of salt including inner salts. Among the new β-lactam salts of the present invention, non-toxic, pharmaceutically acceptable salts of the acid carboxyl group, such as the sodium, potassium, magnesium, calcium, aluminum and ammonium salts and non-toxic substituted ammonium salts, with amines, such as di- and tri-lower alkylamines, procaine, dibenzylamine, N,N'-dibenzylethylenediamine, N-benzyl-β-phenylethylamine, N-methyl- and N-ethyl-morpholine, 1-ephenamine, dehydroabietylamine, N,N'-bis-dehydroabietylethylenediamine, N-lower alkyl-piperidines and other amines which can be used for the formation of salts of penicillins or cephalosporins, are particularly important and are preferred.

The new free β-lactams of the general formula (I) and their salts can be interconverted in any suitable manner; methods for such interconversion are known in the art.

Preferred compounds of the present invention with the Z-configuration are those wherein Z denotes a hydrogen atom or a methoxy group,
X denotes a sulphur atom,
T denotes a radical of the formula $-CH_2OCOCH_3$, $-CH_2-N^{\oplus}$⟨pyridine⟩$-CONH_2$, $-CH_2OCONH_2$ and A denotes a radical of the formula in which $R^1$, $R^2$, $R^3$ and $R^4$ have the abovementioned meanings.

The particular Z- and E-forms of the same structural formula are as a rule substances which have a different activity and which can be prepared separately from one another or together.

According to the present invention we further provide a process for the production of a compound of the present invention, in which a compound of the general formula $$A-CH= \underset{\underset{NH_2}{\overset{N}{\diagdown}\overset{S}{\diagup}}}{\overset{COOH}{\diagup}} \quad (II)$$

wherein

A has the abovementioned meaning, and in which the amino group is in the protected or unprotected form, is reacted, after the carboxyl group has been activated by being converted into a mixed anhydride thereof (for example using ethyl or isobutyl chloroformate), or after being converted into an acid halide thereof, or after being converted into an activated ester thereof (using, for example, N-hydroxysuccinimide or dicyclohexylcarbodiimide), with a compound of the general formula (III)

or a monosilyl or disilyl form thereof or an ester thereof which can be split, wherein Y and Z have the abovementioned meanings, and, if appropriate, the protective group is then removed.

Preferably, the compound of the formula (II) is reacted, after the carboxyl group has been activated with phosphorus oxychloride or phosphorus pentachloride, or in the form of an ester with an alcohol of the formula

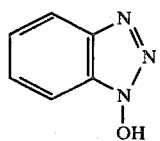  (IV)

with a compound of the formula (III) without prior introduction of an amino-protective group.

Certain compounds of the formula (I) according to the present invention may be converted into other compounds of the invention by a process in which a compound of the formula (I) in which T denotes —CH$_2$—OCO—lower alkyl (in particular —CH$_2$—OCOCH$_3$) is reacted with a nucleophile, for example

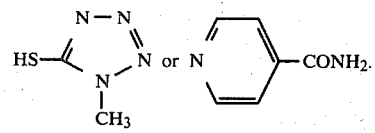

Other compounds of the formula (I) according to the present invention may be interconverted by a process in which a compound of the general formula (I) in which T denotes —CH$_2$OH is reacted with O=C=NSO$_2$Cl or O=C=N—COCCl$_3$ and the SO$_2$Cl group or —COCCl$_3$ group is then split off.

Further compounds of the formula (I) according to the present invention may be interconverted by a process in which a compound of the formula (I) in which Z denotes a hydrogen atom and which is in the form of its free acid, its salt or an ester thereof which can be split is reacted with a hypochlorite (for example (CH$_3$)$_3$COCl) in the presence of an alcoholate (preferably a methanolate, for example LiOCH$_3$) and, if appropriate, the protective group is removed.

The compounds of the formula (II) which are required for the preparation of the compounds according to the invention and which have not yet been described in the literature can be prepared by a number of processes. It has been found that the following three processes are most appropriate. According to process (1), a compound of the general formula

  (V)

in which
A has the abovementioned meaning and
R$^{10}$ denotes a C$_1$ to C$_4$ alkyl group, preferably an ethyl group, is prepared, in a first step, by condensation of a compound of the general formula Cl—CH$_2$—CO—CH$_2$—COOR$^{10}$  (VI)

in which

R$^{10}$ has the abovementioned meaning, with a carbonyl compound of the general formula

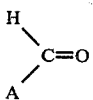  (VII)

in which
A has the abovementioned meaning.

A number of processes have been described for this reaction in the literature, but it has been found that the process in J. Amer. Chem. Soc. 66, 1933 (1944), which has been tested on only one example and which uses the piperidine/glacial acetic acid catalyst system, can be employed for the synthesis of a large number of compounds of the formula (V). This process can be carried out in various solvents under various conditions (for example benzene/water separator/reflux or dimethylformamide/drying agent, for example molecular sieve/50°). The reaction of a compound of the formula (V) with thiourea in a polar solvent (such as acetonitrile) but preferably in a solvent containing hydroxyl groups (such as methanol or ethanol) or a solvent mixture (such as ethanol/water or tetrahydrofuran/water) in a temperature range between 0° and 100° C. (preferably between 20° and 50° C.) if appropriate with the addition of a buffer (such as sodium acetate) leads to a compound which, in the form of the free base, corresponds to the general formula

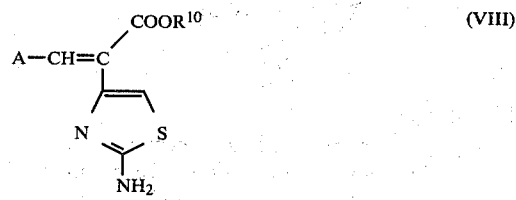  (VIII)

in which
A and R$^{10}$ have the abovementioned meanings.

A compound of the formula (VIII) can be isolated either in the form of the free base corresponding to formula (VIII) as shown or in the form of the hydrochloride thereof. It can be converted into a carboxylic acid of the formula (II) by alkaline ester-hydrolysis with, for example, 2 N NaOH in methanol, ethanol or dioxane as the solvent, at a temperature from 0° to the reflux temperature.

According to process variant (2), a compound of the formula (VIII) is obtained by a route which in principle differs from route (1) only by the sequence of the steps. The condensation product of formula (X) of ethyl acetoacetate of formula (IX) and a carbonyl compound of the formula (VII) reacts with bromine to give a 1,4-dibromide of formula (XI) as indicated by the following reaction scheme:

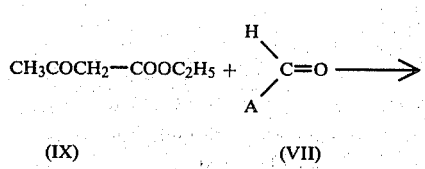

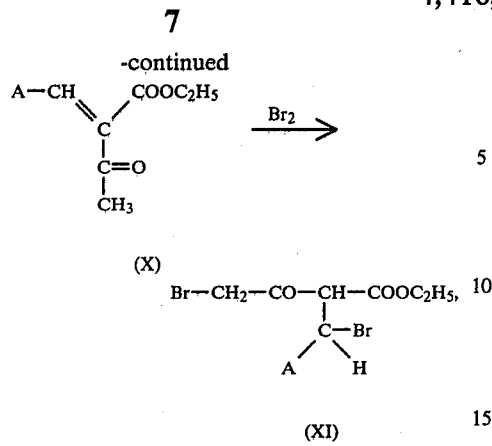

(X)

$$Br-CH_2-CO-CH-COOC_2H_5,$$

(XI)

in which

A has the abovementioned meaning. The reaction proceeds most advantageously when it is carried out at a temperature between −10° and 0° C. in a nonpolar solvent (such as methylene chloride, chloroform or toluene). A compound of the formula (XI) can be reacted with thiourea under the conditions already mentioned to give a compound of the formula (VIII), with simultaneous cyclization and elimination of HBr.

According to process variant (3), the compound of formula (II) having an amino group in protected form may be prepared by a process in which a compound of the general formula

(XII)

in which $R^{10}$ has the abovementioned meaning and
$R^{11}$ represents an amino-protective group (such as a formyl or tert.-butoxycarbonyl group), is reacted with a phosphonate of the general formula

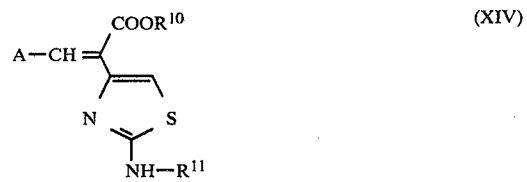

(XIII)

in which

A and $R^{10}$ have the abovementioned meanings, the compound of formula (XIII) is deprotonated with a base (such as sodium hydride, lithium diisopropylamide, lithium hydride, butyl-lithium or potassium tert.-butanolate) in an organic solvent (such as tetrahydrofuran) to give a compound of the general formula

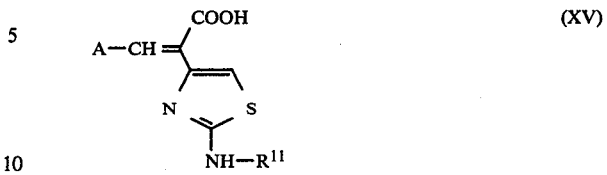

(XIV)

in which $R^{10}$ and $R^{11}$ have the abovementioned meanings, and the compound of formula (XIV) is subjected to alkaline ester-hydrolysis to give a carboxylic acid of the general formula (XV)

in which $R^{11}$ has the abovementioned meaning, (the compound of formula (XV) being the compound of formula (II) having a protected amino group). The compound of formula (XV), as described for compounds of the formula (II), can then be activated and reacted with a compound of the formula (III), a compound of the formula (I) being obtained after the protective groups have been split off.

It is furthermore possible to change the substituent A at one of the synthesis intermediate stages described.

If the compounds according to the invention are to be prepared as a single E- or Z-isomer, these isomers can be separated at any of the synthesis intermediate stages corresponding to compounds of formulae (V), (VIII) or (II) which have been described, with the aid of customary separation methods (such as distillation, crystallization or chromatography) or by selective chemical reaction of only one isomer to give the product of the next synthesis stage.

In a number of cases, it is furthermore possible to achieve isomerization, i.e. conversion of one isomer into the other by treatment with acids or with bases in a polar organic or aqueous-organic or aqueous solvent (such as HCl in ethanol or dilute sodium hydroxide solution).

The compounds according to the invention exhibit a broad antibacterial spectrum against Gram-positive and Gram-negative germs, in particular against Enterobacteriaceae, above all against those with β-lactamase formation.

Furthermore, the compounds according to the invention improve the growth and feed utilization in animals and can be used as antioxidants.

The compounds according to the invention display a powerful and broad antimicrobial activity, coupled with low toxicity. These properties enable them to be used as chemotherapeutic active compounds in medicine and as substances for preserving inorganic and organic materials, especially organic materials of all kinds, for example polymers, lubricants, paints, fibers, leather, paper and timber, and foodstuffs and water.

The compounds according to the invention are active against a very broad spectrum of microorganisms. With their aid, it is possible to combat Gram-negative and Gram-positive bacteria and bacteria-like microorganisms and to prevent, alleviate and/or cure illnesses caused by these pathogens.

The compounds according to the invention are particularly active against bacteria and bacteria-like microorganisms. They are therefore particularly suitable, in human medicine and veterinary medicine, for the prophylaxis and chemotherapy of local and systemic infections caused by these pathogens.

For example, local and/or systemic illnesses which are caused by the following pathogens or by mixtures of the following pathogens can be treated and/or prevented:

Micrococcaceae, such as Staphylococci, for example *Staphylococcus aureus, Staph. epidermis* and *Staph. aerogenes,* and *Gaffkya tetragena* (Staph. = Staphylococcus); Lactobacteriaceae, such as Streptococci, for example *Streptococcus pyogenes,* α- and β-haemolysing Streptococci, non-(γ-)-haemolysing Streptococci, *Str. viridans* and *Str. faecalis* (Enterococci), and *Diplococcus pneumoniae* (Pneumococci) (Str. = Streptococcus); Enterobacteriaceae, such as Escherichiae bacteria of the Coli group: Escherichia bacteria, for example *Escherichia coli,* Enterobacter bacteria, for example *E. aerogenes* and *E. cloacae,* Klebsiella bacteria, for example *K. pneumoniae,* and Serratia, for example *Serratia marcescens* (E. = Enterobacter) (K. = Klebsiella), and Proteae bacteria of the Proteus group: Proteus, for example *Pr. vulgaris, Pr. morganii, Pr. rettgeri* and *Pr. mirabilis* (Pr. = Proteus); Pseudomonadaceae, such as Pseudomonas bacteria, for example *P. aeruginosa* (P. = Pseudomonas); and Bacteroidaceae, such as Bacteroides bacteria, for example *B. fragilis* (B. = Bacteroides).

The above list of pathogens is purely illustrative and is in no way to be interpreted as restrictive.

Examples which may be mentioned of illnesses which can be prevented, alleviated and/or cured by the compounds according to the invention are: illnesses of the respiratory tract and of the pharyngeal cavity; otitis; pharyngitis; pneumonia; peritonitis; pyelonephritis; cyctitis; endocarditis; systemic infections; bronchitis; arthritis; and local infections.

As stated above, the invention also relates to the use in human and veterinary medicine of the compounds of the invention.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical composition according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic, The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitan esters), microcrystalline cellulose, aluminum metahydroxide, bentonite, agar-agar and tragacanth or mixtures thereof.

All the pharmaceutical compositions according to the invention can also contain colouring agents and preservatives as well as perfumes and flavoring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampules. Some of these forms may be made up for delayed release of the active ingredient. Some, such as capsules, include a protective envelope which renders the portions of the medicament physically discrete and coherent.

The preferred daily dose for administration of the medicaments of the invention is 0.5 g to 10 g of active ingredient.

The production of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously and intravenously), rectally or locally, preferably orally or parenterally, especially intravenously or intramuscularly. Preferred pharmaceutical compositions and medicaments are therefore those adapted for administration such as oral or parenteral administration. Administration in the method of the invention is preferably oral or parenteral administration.

In general it has proved advantageous to administer amounts of from 5 mg to 1000 mg/kg, preferably 10 mg to 200 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, while in other cases the upper limit mentioned must be exceeded to achieve the desired results. Where larger amounts are administered it can be advisable to divide these into several individual administrations over the course of the day. An individual administration preferably contains 1 mg to 250 mg/kg, preferably 3 mg to 60 mg/kg, of body weight of the active ingredient.

When used as feed additives, the compounds of the present invention can be administered in the customary concentrations and formulations together with the feed or with the feed formulations or with the drinking water. By this means, it is possible to prevent, alleviate and/or cure an infection by Gram-negative or Gram-positive bacteria and also to achieve promotion of growth and better utilization of the feed.

The new compounds are distinguished by powerful antibacterial actions, which have been tested in vivo and in vitro, and by their ease of absorption on oral administration.

For the purpose of broadening the action spectrum and in order to achieve a more powerful action, especially in the case of bacteria which form $\beta$-lactamase, the compounds according to the invention can be combined with other antimicrobial active compounds, for example with penicillins which are particularly resistant to penicillinase. Such a combination would be, for example, that with oxacillin or dicloxacillin.

For the purpose of broadening the action spectrum and in order to achieve a more powerful action, the compounds according to the invention can also be combined with aminoglycoside antibiotics, such as gentamicin, sisomicin, kanamicin, amikacin or tobramicin.

The compounds according to the invention prevent the degradation of, for example, penicillins by $\beta$-lactamases, which usually hydrolyze sensitive penicillins and thus render them inactive. If an amount of 100 mg of mezlocillin per milliliter is added to a crude extract of $\beta$-lactamase obtained from E. coli A 261, the penicillin is completely inactivated within 60 minutes. However, if a combination of 100 mg of mezlocillin plus 100 mg of the compound from Example 23 is added, the mezlocillin remains completely antibacterially active.

The activity of the $\beta$-lactam antibiotics according to the invention can be demonstrated, by way of example, by the following in vitro experiments:

In vitro experiments

The antibacterial action of the compounds of following Examples 18 and 23, which can be regarded as typical representatives of the compounds according to the invention, was tested in an agar dilution test under German DIN standard conditions. The concentration was 100 mcg per milliliter of agar. A complete inhibition of growth was found with the following strains of bacteria:

E. coli T 7, Klebsiella 57 US, *Serratia macescens* 16001, Providencia 12012, *Proteus morganii* 932, *Proteus vulgaris* 1017, *Proteus rettgeri, Enterobacter aerogenes* 55 US, *Pseudomonas aeruginosa* W, *Bacteroides fragilis* 012 999, *Staphylococcus aureus* 133 and *Enterococcus* ATCC 9790.

The following examples illustrate processes for the production of compounds of the present invention.

In the examples all temperature given are expressed in degrees centigrade.

The determination of the double bond configuration in the compounds according to the invention was carried out with the aid of $^{13}$C-nuclear magnetic resonance spectroscopy. It is known that in tri-substituted olefins of the type of formula (XVI)

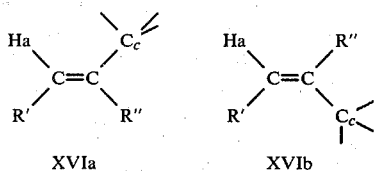

XVIa    XVIb wherein

R' and R" represent organic radicals, the $^{3}$I-Ha $C_c$-hetero-coupling is always substantially greater if Ha and $C_c$ are in the trans-position (formula (XVIb)) than if they are in the corresponding cis-position (formula (XVIa)). This observation was used to allocate the configuration in one of the precursors of formulae (V), (VIII) or (II) of the compounds according to the invention.

EXAMPLE 1

2-(2-Bromo-2-phenyl-methyl)-3-oxo-4-bromobutyric acid ethyl ester.

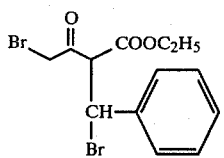

430 g of bromine were added dropwise to 595 g of 2-benzylideneacetoacetic acid ethyl ester in 3 liters of methylene chloride at −10° to −5°. The mixture was subsequently stirred at room temperature for one hour, the solvent was then stripped off at room temperature, ligroin was added to the residue and the residue was decanted. Ligroin was again added to the residue and the mixture was left to stand overnight. The product which had precipitated was filtered off and recrystallized twice from ligroin. Yield: 23.5%, melting point: 99° to 101°.

IR (Nujol): 1738, 1712, 1575, 1460, 1320, 1290, 1270, 1208, 1181, 1143, 1092, 1030, 1005 cm$^{-1}$.

NMR (CDCl$_3$): δ=0.91[3] t, J=7 Hz, 3.92[2] q, J=7 Hz, 4.25[2], s, 4.83[1] d, J=11 Hz, 5.54 [1] d, J=11 Hz, 7.36[5] m ppm.

EXAMPLE 2

2-(2-Aminothiazol-4-yl)-3-phenylpropenoic acid ethyl ester (E-isomer)

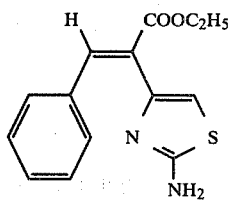

323.5 g of the substance prepared according to Example 1 were dissolved in 5 liters of ethanol. 65 g of thiourea were introduced in portions into this solution at 50°. The mixture was subsequently stirred at 50° for 2 hours, the solvent was stripped off and the oily residue was taken up in water. After the mixture had been adjusted to pH 9 with concentrated ammonia solution, it was extracted three times with ethyl acetate. The purified extracts were dried over magnesium sulphate and evaporated. The residue was recrystallized from ethanol and acetone. Yield: 45%, melting point: 162°.

IR (Nujol): 1680, 1620, 1520, 1365, 1260, 1205 cm$^{-1}$.

NMR (CDCl$_3$+DMSO): δ=7.75[1] s, 7.22[5] s, 6.25[1] s, 6.19[2] s broad, 4.21[2] q, J=7 Hz, 1.25[3] t, J=7 Hz ppm.

Calculated: C 61.3 H 5.1 N 10. S 11.7. Found: C 61.0 H 5.3 N 10.2 S 11.2.

EXAMPLE 3

2-(2-Aminothiazol-4-yl)-3-phenylpropenoic acid (E-isomer)

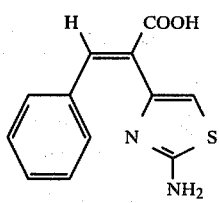

20 g of the compound prepared according to Example 2, dissolved in 250 ml of methanol, were added to 222 ml of 1 N sodium hydroxide solution. After the mixture had been stirred overnight at room temperature, the methanol was stripped off. The aqueous phase which remained was adjusted to pH 6.5 with 2 N hydrochloric acid and extracted twice with ethyl acetate and the extract was then slowly adjusted to pH 4. The product which had precipitated was filtered off and recrystallized from ethanol. Yield: 75.2%, melting point: 206° to 207° (decomposition).

IR (Nujol): 1660, 1620, 1589, 1321, 1226, 1196 cm$^{-1}$.

NMR (CDCl$_3$+DMSO): δ=7.67[1] s, 7.23[5] s, 6.90[2] s broad, 6.25[1] ppm.

Calculated: C 58.5 H 4.1 N 11.4 S 13.0. Found: C 58.0 H 4.2 N 11.2 S 12.7.

EXAMPLE 4

2-(2,6-Dichlorobenzylidene)-3-oxo-4-chlorobutyric acid ethyl ester

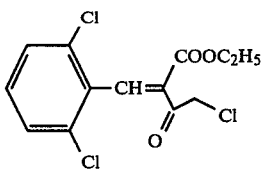

10 g of 4-chloroacetoacetic acid ethyl ester, 10.5 g of 2,6-dichlorobenzaldehyde, 0.7 ml of glacial acetic acid and 0.35 ml of piperidine were dissolved in 15 ml of benzene. The solution was boiled for 6 hours using a water separator and was then allowed to cool, 100 ml of ether were added and the mixture was extracted in each case once with saturated sodium bicarbonate solution, water, 1 N citric acid solution and again with water. The organic phase was dried over magnesium sulphate and concentrated. The oil which remained was subjected to incipient distillation under a high vacuum. The product remained as an oily residue which contained the two isomers, according to gas chromatography and NMR, as a 3:1 mixture.

Yield: 64.5%.

The Z-isomer, which was present as the main component, could be crystallized out of this mixture in a pure form using isopropanol. Yield: 5.5 g, melting point: 74° to 76°. A 1:1 E/Z mixture which could no longer be crystallized remained in the mother liquor.

(a) Z-isomer:

IR (KBr): 1727, 1708, 1619, 1557, 1441, 1430, 1377, 1232 cm$^{-1}$:

NMR (CDCl$_3$): δ=7.82[1] s, 7.32[3] m, 4.60[2] s, 4.12[2] q, J=7 Hz, 0.98[3] t, J=7 Hz ppm.

Calculated: C 48.6 H 3.4 Cl 33.1. Found: C 48.4 H 3.4 Cl 33.1.

(b) E-isomer

NMR (CDCl$_3$): δ=7.80[1] s, 7.32[3] m, 4.43[2] s, 4.40[2] g J=7 Hz, 1.38[3] t, J=7 Hz ppm.

EXAMPLE 5

2-(2-Aminothiazol-4-yl)-3-(2,6-dichlorophenyl)-propenoic acid ethyl ester hydrochloride (Z-isomer)

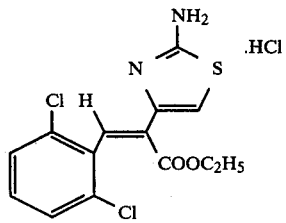

52.2 g of the crude E/Z mixture finally produced as described in Example 4 and 12.3 g of thiourea were dissolved in 500 ml of ethanol. After 5 hours, the solution was heated to 50° C. and was then left to stand at room temperature for 16 hours. After the product had been filtered off, a second crystalline fraction of the same purity could be crystallized by concentration of the mother liquor. The product was recrystallized from ethanol.

Yield: 36.5%, melting point: 250° C.

IR (Nujol): 1710, 1635, 1588, 1315, 1240, 1160, 1020 cm$^{-1}$.

NMR (DMSO): δ=8.41 [3] s broad, 7.62 [1] s, 7.50 [3] m, 7.07 [1] s, 4.04 [2] q, J=7 Mz, 0.91 [3] t, J=7 Hz ppm.

Calculated: C 44.3 H 3.4 N 7.4 S 8.4 Cl 28.1. Found: C 44.2 H 3.6 N 6.4 S 8.0 Cl 27.8.

EXAMPLE 6

2-(2-Aminothiazol-4-yl)-3-(2,6-dichlorophenyl)-propenoic acid (Z-isomer)

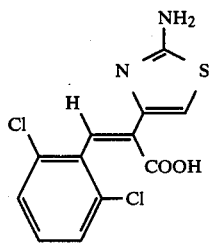

6.5 g of 45 percent strength sodium hydroxide solution were added to a solution of 10 g of the ester prepared according to Example 5 in a mixture of 50 ml of dioxane and 20 ml of water and the mixture was then boiled under reflux for 56 hours. 100 ml of water were added, the dioxane was stripped off and the aqueous phase was adjusted to pH 7.5 with 2 N hydrochloric acid. After the mixture had been extracted twice with ethyl acetate, the extract was adjusted to pH 2 and the product which had precipitated was filtered off. Yield: 88.7%, melting point: 163° to 165° (decomposition).

IR (Nujol): 1642, 1601 (shoulder), 1580, 1405, 1285, 1198 cm$^{-1}$.

NMR (DMSO): δ=7.45[4] m, 7.16[2] s, broad, 6.90 [1] s ppm.

EXAMPLE 7

2-(4-Chlorobenzylidene)-3-oxo-4-chlorobutyric acid ethyl ester

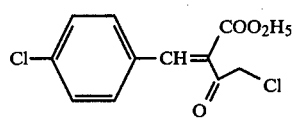

25.7 g of 4-chloroacetoacetic acid ethyl ester, 23.9 g of 4-chlorobenzaldehyde, 0.7 ml of piperidine and 18 ml of glacial acetic acid were dissolved in 15 ml of benzene. The solution was boiled for 5 hours, using a water separator, and was allowed to cool, and 300 ml of ether were added. After the mixture had been washed three times with water, it was dried over magnesium sulphate and the solvent was evaporated off. The residue was distilled under a high vacuum. The product obtained was a Z/E mixture in a ratio of 3/1. Yield: 23.4%, boiling point 0.5: 161° to 165°.

IR (film): 1720, 1695 (shoulder), 1622, 1592, 1494, 1395, 1315, 1290, 1260, 2000 cm$^{-1}$.

NMR (CDCl$_3$):

(a) Z-isomer δ=7.75 [1] s, 7.30 [4] s, 4.32 [2] s, 4.30 [2] q, J=7 Hz, 1.31 [3] t, J=7 Hz ppm.

(b) E-isomer δ=7.66 [1] s, 7.36 [4] s, 4.50 [2] s, 4.30[2] q, J=7 Hz, 1.25 [3] t, J=7 Hz ppm.

Calculated: C 54.4 H 4.2 Cl 24.7. Found: C 54.0 H 4.2 Cl 24.8.

EXAMPLE 8

2-(2-Aminothiazol-4-yl)-3-(4-chlorophenyl)-propenoic acid ethyl ester

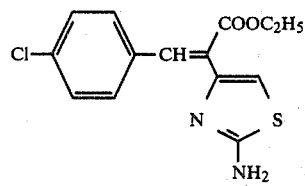

10.5 g of the final substance prepared as described in Example 7 and 2.8 g of thiourea were dissolved in 275 ml of ethanol and the solution was warmed to 50° for 2 hours. After the solvent had been evaporated off, ethyl acetate and water were added to the oil which remained and the solution was adjusted to pH 1 with hydrochloric acid. The ethyl acetate phase was separated off and dried over magnesium sulphate and the solvent was evaporated off. The viscous oil which remained consisted of impure product. The acid aqueous phase was adjusted to pH 11 with concentrated ammonia solution and was then extracted three times with chloroform. After the mixture had been dried over magnesium sulphate and the chloroform had been evaporated off, the pure E-isomer of the product could be crystallized with ethanol. Further E-isomer and also Z-isomer of the title compound could be isolated, in each case in a pure form, by medium pressure chromatography of the mother liquor.

(a) E-isomer:

Melting point: 119° to 121° (decomposition)

IR (Nujol): 3350, 3240, 3080, 1695, 1630, 1620, 1530, 1490, 1270, 1205, 1182, 1098 cm$^{-1}$.

NMR (CDCl$_3$): δ=7.88 [1] s, 7.26 [3] m, 6.42 [4] s, 5.50 [2] s broad, 4.33 [2] q, J=7 Hz, 1.33 [3] t, J=7 Hz ppm.

Calculated: C 54.5 H 4.2 N 9.1 S 10.4 Cl 11.5. Found: C 53.4 H 4.5 N 9.2 S 10.8 Cl 11.4.

(b) Z-isomer:

Melting point: 114° to 116° (decomposition)

IR (Nujol): 3360, 3250, 3100, 1698, 1630, 1535, 1222, 1100, 1030, 1010 cm$^{-1}$.

NMR (CDCl$_3$): δ=7.45 [1] s, 7.26 [4] m, 6.55 [1] s, 5.20 [2] s, broad, 4.25 [2] q, J=7 Hz, 1.18 [3] t, J=7 Hz ppm.

Calculated: C 54.5 H 4.2 N 9.1 S 10.4 Cl 11.5. Found: C 53.5 H 4.3 N 8.6 S 9.8 Cl 11.8.

EXAMPLE 9

2-(2-Aminothiazol-4-yl)-3-(4-chlorophenyl)-propenoic acid (E-isomer)

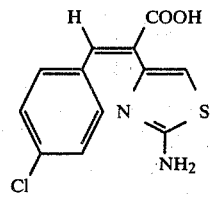

10 g of the pure E-isomer prepared as described in Example 8 were dissolved in a mixture of 50 ml of methanol and 20 ml of water. 20 ml of 2 N sodium hydroxide solution were added to the solution and the mixture was stirred at room temperature overnight. The methanol was stripped off, the aqueous phase was adjusted to pH 3 with 2 N hydrochloric acid and the product which has precipitated was filtered off. It was recrystallized from ethanol.

Yield: 66.6%, melting point: 225° (decomposition).

IR (Nujol): 1650, 1620, 1585, 1338 cm$^{-1}$.

NMR (DMSO): δ=7.72 [1] s, 7.33 [4] m, 7.0–7.8 [3] broad, 6.40 [1] s ppm.

EXAMPLE 10

2-(2-Furylidene)-3-oxo-4-chlorobutyric acid ethyl ester

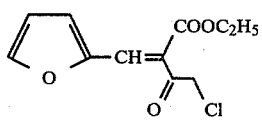

200 g of 4-chloroacetoacetic acid ethyl ester, 125.6 g of freshly distilled furfural, 2.6 ml of piperidine and 7 ml of glacial acetic acid were dissolved in 120 ml of benzene and the solution was boiled for 5 hours, using a water separator. 1 liter of ether was added to the cooled solution and the mixture was then extracted in each case once by shaking with saturated sodium bicarbonate solution, water, 2 M citric acid solution and again with water. After the extract had been dried over magnesium sulphate and concentrated, an oil was obtained and was subjected to incipient distillation under a high vacuum. The product remained as a viscous oil and the E/Z isomer ratio was 4:1. Yield: 86.8%.

IR (Nujol): 1720, 1678, 1620, 1450, 1415, 1355, 1303 cm$^{-1}$.

NMR (CDCl$_3$): (signals of equivalent protons from isomeric compounds are separated by a "/"): δ=7.50 [2] m, 7.03/6.89 [1] d, J=7 Hz, 6.57 [1] m, 4.48/4.50 [2] s, 4.43/4.32 [2] q, J=7 Hz, 1.40/1.34 [3] t, J=7 Hz ppm.

Calculated: C 54.4 H 4.6 Cl 14.6. Found: C 54.3 H 4.5 Cl 14.8.

EXAMPLE 11

2-(2-Aminothiazol-4-yl)-3-(2-furyl)-propenoic acid ethyl ester hydrochloride (E-isomer)

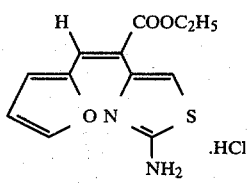

32.2 g of the isomer mixture prepared as described in Example 10 and 10 g of thiourea were dissolved in 850 ml of ethanol. The solution was heated to 50° for 4 hours and was then left to stand at room temperature for 16 hours. The product which had precipitated was filtered off. Further product of the same purity could be obtained by concentrating the mother liquor. After recrystallization of the product from ethanol, the E-isomer, containing about 10% of the Z-isomer, was obtained.

Yield: 65.4%, melting point >250°. The E-isomer could be obtained in a pure form by repeated recrystallization from ethanol.

IR (Nujol): 1679, 1620, 1300, 1270, 1222, 1156, 1080, 1050, 1025 cm$^{-1}$.

NMR (DMSO): δ=6.6–8.2 [1] broad, NH, 7.86 [1] d, J=2 Hz, 7.75 [1] s, 7.0 [1] d, J=4 Hz, 6.90 [1] s, 6.66 [1] dd, J=2 Hz, J=4 Hz, 4.20 [2] q, J=7 Hz, 1.25 [3] t, J=7 Hz ppm.

Calculated: C 47.9 H 4.4 N 9.3 S 10.7 Cl 11.8. Found: C 47.8 H 4.5 N 9.1 S 10.2 Cl 11.7.

EXAMPLE 12

2-(2-Aminothiazol-4-yl)-3-(2-furyl)-propenoic acid (E-isomer)

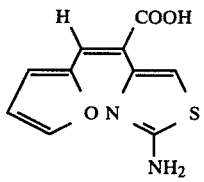

8.5 g of the product prepared as described in Example 11 were dissolved in a mixture of 50 ml of methanol and 50 ml of water. The solution was brought to pH 13 with 2 N sodium hydroxide solution and was stirred at room temperature for 5 hours. The methanol was then stripped off and the aqueous solution was adjusted to pH 7.5 with 2 N hydrochloric acid and extracted twice with ethyl acetate. The extract was adjusted to pH 3 and the product was filtered off and recrystallized from ethanol. Yield: 64.3%, melting point: 201° (decomposition).

IR (Nujol): 1630, 1598, 1570, 1540, 1330, 1280 cm$^{-1}$.

NMR (DMSO): δ=7.84 [1] d, J=1.5 Hz, 7.64 [1] s, 7.50 [3] s broad, 6.65 [1] s, 6.61 [2] s, broadened ppm.

Calculated: C 50.8 H 3.4 N 11.9 S 13.5. Found: C 50.4 H 3.4 N 11.6 S 12.8.

EXAMPLE 13

2-(3-Thienylidene)-3-oxo-4-chlorobutyric acid ethyl ester

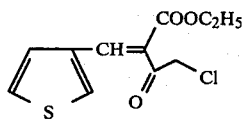

55.3 g of 4-chloroacetoacetic acid ethyl ester, 41 g of thiophene-3-aldehyde, 3.8 ml of glacial acetic acid and 1.5 ml of piperidine were dissolved in 30 ml of benzene. The solution was boiled for 7 hours, using a water separator, and, after the solution had been cooled, 400 ml of ether were added and the mixture was extracted three times with water. After the extract had been dried over sodium sulphate and the solvent had been evaporated off, the crude product was subjected to incipient distillation and the residue was then purified over a short silica gel column (70 to 230 mesh) (Mobile phase: petroleum ether/ether 8/2). The E/Z mixture was obtained as an oil.

Yield: 63%.

IR (film): 1720, 1690, 1609, 1265, 1240 cm$^{-1}$.

NMR (CDCl$_3$): δ=7.54–7.83 [2] m, 6.95–7.50 [2] m, 4.52/4.45 [2] s, 4.35/4.26 [2] q, J=7 Hz, 1.27/1.32 [3] t, J=7 Hz ppm (the signals which arise from isomeric compounds and correspond to one another are separated by a "/").

Calculated: C 51.1 H 4.3 S 12.4 Cl 13.7. Found: C 51.7 H 4.5 S 12.4 Cl 12.6.

EXAMPLE 14

2-(2-Aminothiazol-4-yl)-3-(3-thienyl)-propenoic acid ethyl ester hydrochloride (E-isomer)

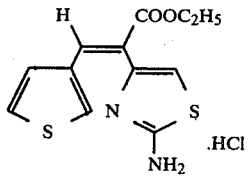

22 g of the E/Z mixture prepared as described in Example 13 and 6.5 of thiourea, dissolved in 100 ml of ethanol, were heated to 50° for 2.5 hours. The solution was evaporated, a little water and ethyl acetate were added to the residue and the product was filtered off.

Yield: 22%, melting point: 213° to 215° (decomposition).

IR (Nujol): 1685, 1620, 1278 cm$^{-1}$.

NMR (CD$_3$OD): δ=8.18 [2]s, 7.87 [1] dd, J=2 Hz, J=4 Hz, 7.53 [1] dd, J=4 Hz, J=6 Hz, 6.95 [1] dd, J=2 Hz, J=6 Hz, 6.86 [1] s, 4.32 [2] q, J=7 Hz, 1.32 [3] t, J=7 Hz ppm.

Calculated: C 45.5 H 4.1 N 8.8 S 20.2 Cl 11.2. Found: C 45.1 H 4.4 N 8.5 S 19.5 Cl 10.9.

EXAMPLE 15

2-(2-Aminothiazol-4-yl)-3-(3-thienyl)-propenoic acid (E-isomer)

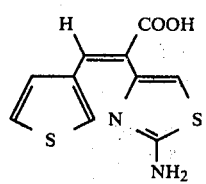

8 ml of 2 N sodium hydroxide solution were added to 3.3 g of the product prepared as described in Example 14, dissolved in 10 ml of methanol. The solution was left to stand overnight at room temperature and the methanol was then stripped off and the residue was dissolved in water. The pH was adjusted to 8 with 2 N hydrochloric acid and the aqueous solution was extracted three times with acetic acid. The product was then precipitated by adjusting the pH to 3 and was filtered off.

Yield: 50.5%, melting point: 172° to 175° (decomposition).

IR (KBr): 1628, 1367, 1262, 1028 cm$^{-1}$.

NMR (DMF): δ=8.5, N-H, very broad, 7.93 [1] s, broadened, 7.86 [1] dd, J$_1$=1.5 Hz, J$_2$=3 Hz, 7.54 [1] dd, J$_3$=1 Hz, J$_4$=6 Hz, 6.91 [1] dd, J$_4$=6 Hz, J$_1$=1.5 Hz, 6.70 [1] s ppm.

Calculated: C 47.6 H 3.2 N 11.1 S 25.4. Found: C 47.2 H 3.1 N 11.4 S 25.3.

EXAMPLE 16

Sodium
E-7-[2-(2-aminothiazol-4-yl)-2-benzylideneacetamido]-3-acetoxymethyl-3-cephem-4-carboxylate

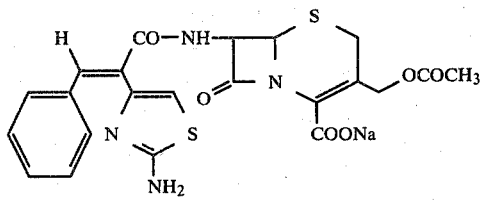

A suspension of 4.9 g of the product as described in Example 3 in 200 ml of ethyl acetate was cooled to 0° to 5° and 3.8 g of phosphorus oxychloride were added. After 30 minutes, 3.3 g of trimethylsilylacetamide, dissolved in 5 ml of ethyl acetate, were added, and a further 3.8 g of phosphorus oxychloride were then added. The mixture was subsequently stirred at 0° for 15 minutes and 1.8 ml of dimethylformamide was then added. After a further 40 minutes, the mixture was cooled to −10° and added dropwise to a solution, which had been cooled to −5°, of 5.44 g of 7-aminocephalosporanic acid and 4 g of sodium bicarbonate in a mixture of 100 ml of water and 75 ml of acetone. The mixture was subsequently stirred for 2 hours, during which the pH value was kept at 6 with saturated sodium bicarbonate solution. The solution was filtered, the aqueous phase was separated off and washed once with ethyl acetate, ethyl acetate was added and the mixture was adjusted to pH 3.5. The ethyl acetate was separated off and the aqueous phase was extracted twice more with ethyl acetate. Water was added to the combined ethyl acetate phases and the mixture was brought to pH 7. The aqueous phase was separated off and lyophilized to give 2.0 g of the product.

IR (Nujol): 1750 cm$^{-1}$.

NMR (CD$_3$OD): δ=7.78 [1] s, 7.29 [5] s, 6.32 [1] s, 5.82 [1] d, J=5 Hz, 5.09 [1] d, J=5 Hz, 5.06 [1] d, J=14 Hz, 4.83 [1] d, J=14 Hz, 3.60 [1] d, J=18 Hz, 3.29 [1] d, J=18 Hz, 2.03 [3] s ppm.

EXAMPLE 17

Sodium
E-6-[2-(2-aminothiazol-4-yl)-2-benzylideneacetamido]penam-3-carboxylate

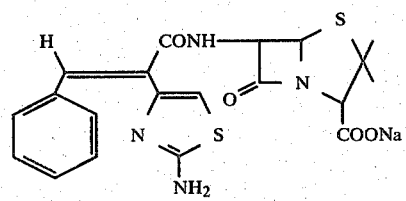

1.9 g of the product obtained as described in Example 3 were reacted, according to the instructions in Example 16, with 6-amino-penicillanic acid instead of 7-aminocephalosporanic acid. 1.4 g of the lyophilized sodium salt were obtained. Melting point: 250°.

IR (KBr): 1761, 1607, 1508 cm$^{-1}$.

NMR (CD$_3$OD): 7.78 [1] s, 7.25 [5] s, 6.33 [1] s, 5.62 [2] s, 4.25 [1] s, 1.58 [6] s ppm.

EXAMPLE 18

Triethylammonium
Z-7-[2-(2-aminothiazol-4-yl)-2-(2,6-dichlorobenzylidene)-acetamido]-3-acetoxymethyl-3-cephem-4-carboxylate

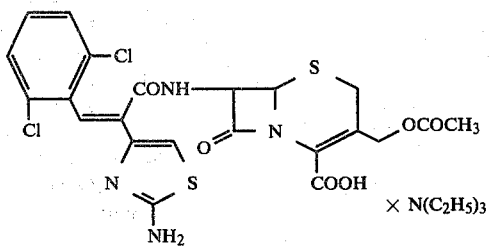

0.68 g of 1-hydroxybenzotriazole and 1.03 g of N,N'-dicyclohexylcarbodiimide were added to a solution of 2.1 g of the product from Example 6 in 15 ml of absolute dimethylformamide and the mixture was stirred at room temperature for 5 hours. The mixture was filtered and a solution of 1.36 g of 7-aminocephalosporanic acid and 2.0 ml of triethylamine in 25 ml of methylene chloride was added dropwise to the mother liquor. The reaction solution was stirred overnight at room temperature and was then evaporated to dryness. The residue was dissolved in a little water and the solution was filtered at pH 7 and then washed several times with ethyl acetate. The aqueous solution was adjusted to pH 4.5 with 2 N hydrochloric acid, and the product which has precipitated was filtered off, washed with water and dried over potassium hydroxide. The crude product was stirred with ethyl acetate for 1 hour and filtered off, the residue was stirred with methanol for 1 hour and filtered off again and the filtrate was evaporated to dryness in the cold. The residue was dried over potassium hydroxide. 0.6 g of the desired product was obtained.

IR (KBr): 1775, 1735, 1675, 1620 cm$^{-1}$.

NMR (CD$_3$OD): δ=7.2–7.44 [4] m, 6.78 [1] s, 5.71 [1] d, J=6 Hz, 5.07 [1] d, J=12 Hz, 5.05 [1] d, J=6 Hz, 4.82 [1] d, J=12 Hz, 3.60 [1] d, J=18 Hz, 3.38 [1] d, J=18 Hz, 2.07 [3] s, 3.23 [6] q, J=7 Hz and 1.32 [9] t, J=7 Hz, ppm.

EXAMPLE 19

E-7-[2-(2-Aminothiazol-4-yl)-2-(2-furylidene)acetamido]-3-acetoxymethyl-3-cephem-4-carboxylic acid

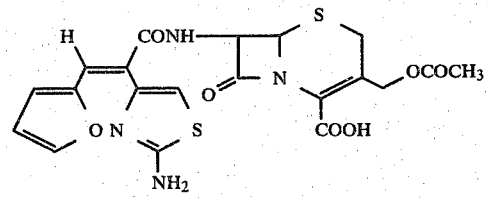

2.0 g of the product prepared according to Example 12 were dissolved in 30 ml of absolute dimethylformamide under nitrogen in a previously thoroughly heated flask. 1.12 g of 1-hydroxybenzotriazole and 1.7 g of N,N'-dicyclohexylcarbodiimide were added to the solution and the mixture was stirred at room temperature for 6 hours. After the dicyclohexylurea had been filtered off, a solution of 2.2 g of 7-aminocephalosporanic acid and 3.4 ml of triethylamine in 20 ml of methylene chloride was added dropwise to the filtrate. The mixture was stirred overnight and then evaporated to dryness and the residue was dissolved at pH 7. After the aqueous solution had been extracted several times with ethyl acetate, it was adjusted to pH 2.5 with 2 N HCl and stirred for 30 minutes. The product was filtered off and dried over KOH. This crude product was stirred with ethyl acetate for 1 hour, filtered off and then dissolved in cold methanol. The product was isolated by filtration and evaporation of the solution.

IR (KBr): 1759, 1612, 1514, 1397, 1249 cm$^{-1}$.

NMR (CD$_3$OD): $\delta$=7.54 [1] s, 7.52 [1] s, 6.60 [1] s, 6.44 [2] m, 5.76 [1] d, J=5 Hz, 5.04 [1] d, J=5 Hz 4.98 [1] d, J=11 Hz, 4.80 [1] d, J=11 Hz, 3.58 [1] d, J=17 Hz, 3.30 [1] d, J=17 Hz, 2.01 [3] s ppm.

EXAMPLE 20

Sodium E-7-[2-(2-aminothiazol-4-yl)-2-(3-thienylidene)acetamido]-3-acetoxymethyl-3-cephem-4-carboxylate

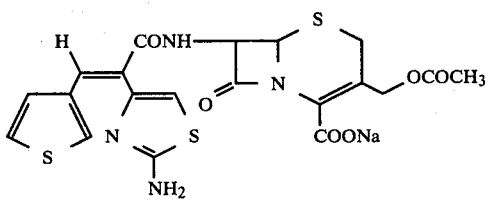

1.0 g of the product prepared according to Example 15 was reacted as described in Example 18. The free acid precipitated at pH 4.5 dissolved in water with 2 N sodium hydroxide solution at pH 6.5 and the solution was then lyophilised. 0.7 g of the desired compound was obtained.

IR (Nujol): 1758, 1605, 1412, 1220 cm$^{-1}$.

NMR (CD$_3$OD): $\delta$=7.76 [1] s, 7.52 [1] d, J=2 Hz, 7.29 [1] dd, J=2 Hz, J=6 Hz, 6.79 [1] d, J=6 Hz, 5.79 [1] d, J=5 Hz, 5.08 [1] d, J=5 Hz, 5.00 [1] d, J=11 Hz, 4.82 [1] d, J=11 Hz, 3.60 [1] d, J=18 Hz, 3.32 [1] d, J=18 Hz, 2.04 [3] s ppm.

EXAMPLE 21

Sodium E-7-[2-(2-aminothiazol-4-yl)-2-(4-chlorobenzylidene)acetamido]-3-acetoxymethyl-3-cephem-4-carboxylate

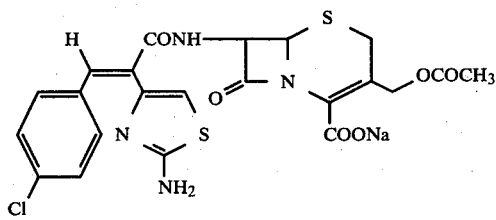

2.0 g of the compound prepared as described in Example 9 were reacted as described in Example 19. The crude product which had been filtered off at pH 2.5 was dissolved in cold methanol and the solution was filtered and evaporated to dryness. The residue was dissolved in water with 2 N sodium hydroxide solution at pH 6.8. 0.9 g of the desired product was isolated by lyophilization of the aqueous solution.

IR (Nujol): 1579, 1610, 1515 cm$^{-1}$.

NMR (CD$_3$OD): $\delta$=7.67 [1] s, 7.25 [4] m, 6.35 [1] s, 5.82 [1] d, J=5 Hz, 5.10 [1] d, J=5 Hz, 5.02 [1] d, J=12 Hz, 4.85 [1] d, J=12 Hz, 3.61 [1] d, J=17 Hz, 3.33 [1] d, J=17 Hz, 2.06 [3] s ppm.

EXAMPLE 22

Sodium E-7-[2-(2-aminothiazol-4-yl)-2-(4-chlorobenzylidene)-acetamido]-penam-3-carboxylate

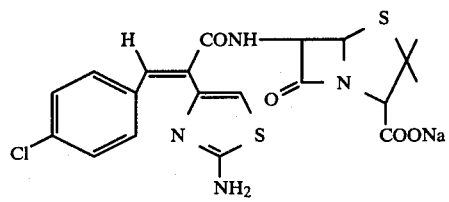

2.3 g of the product from Example 9 were reacted as described in Example 17. 1.0 g of the lyophilized sodium salt was obtained.

IR (Nujol): 1755, 1600 cm$^{-1}$.

NMR (CD$_3$OD): $\delta$=7.71 [1] s, 7.24 [4] m, 6.36 [1] s, 5.59 [2] s, 4.20 [1] s, 1.55 [3] s, 1.54 [3] s ppm.

EXAMPLE 23

Z-6-[2-(2-Aminothiazol-4-yl)-2-(2,6-dichlorobenzylidene)-acetamido]-penam-3-carboxylic acid

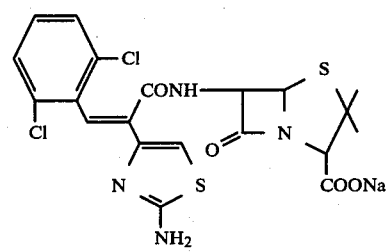

0.9 g of the product from Example 6 were dissolved in 15 ml of absolute dimethylformamide. 0.3 g of hydroxybenzotriazole and 0.44 g of dicyclohexylcarbodiimide were added and the mixture was stirred at room temperature for 5 hours. The mixture was filtered and the mother liquor was added dropwise to a solution of 0.4 g of 6-aminopenicillanic acid and 0.9 ml of triethylamine in 25 ml of methylene chloride. After the mixture had been stirred at room temperature overnight, it was evaporated, water and ethyl acetate were added to the residue and the mixture was adjusted to pH 6.5. The mixture was filtered, the organic phase was separated off and the aqueous phase was washed once more with ethyl acetate. The product phase was then adjusted to pH 2.8 and filtered. 0.5 g of product were thus obtained.

IR (KBr): 1770 (shoulder), 1728, 1637 cm$^{-1}$.

NMR (CD$_3$OD): $\delta$=7.1 [4] m, 6.74 [1] s, 5.52 [1] d, J=6 Hz, 5.45 [1] d, J=6 Hz, 4.31 [1] s, 1.49 [3] s, 1.47 [3] s ppm.

EXAMPLE 24

2-(2,4,6-Trimethylbenzylidene)-3-oxo-4-chlorobutyric acid ethyl ester

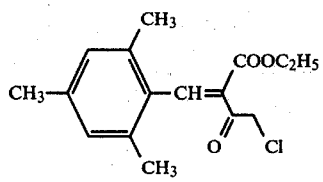

90 g of 2,4,6-trimethylbenzaldehyde, 150 g of 4-chloroacetoacetic acid ethyl ester, 2.6 ml of piperidine and 7 ml of glacial acetic acid were dissolved in 60 ml of benzene and the solution was boiled for 6 hours using a water separator. 200 ml of ethyl acetate were added to the cooled solution, the solution was extracted in each case once with saturated sodium bicarbonate solution, water and 1 M citric acid solution and the extract was dried over magnesium sulphate and evaporated. The crude product was subjected to incipient distillation under a high vacuum in order to free it from excess 4-chloroacetoacetic acid ethyl ester. After chromatography of the product on Silica gel 60 (Merck, 70-230 mesh), 21 g of the E-isomer could be crystallized with isopropanol and 3:1 Z/E mixture remained as the mother liquor in the form of an oil. Total yield: 39%.
E-isomer: melting point 85°.

IR (Nujol): ~1700, 1610, 1310, 1250, 1175, 1135, 1095, 1030, 970 cm$^{-1}$.

NMR (CDCl$_3$): δ=8.02 [1] s, 6.90 [2] s, 4.37 [2] q, J=7 Hz, 4.04 [2] s, 2.32 [3] s, 2.20 [6] s, 1.38 [3] t, J=7 Hz ppm.

Calculated: C 65.2 H 6.5 Cl 12.0. Found: C 65.1 H 6.8 Cl 12.0.

Z-isomer:
NMR (CDCl$_3$): δ=7.98 [1] s, 6.84 [2] s, 4.56 [2] s, 4.06 [2] q, J=7 Hz, 2.32 [3] s, 2.20 [6] s, 0.91 [3] t, J=7 Hz ppm.

EXAMPLE 25

2-(2-Aminothiazol-4-yl)-3-(2,4,6-trimethylphenyl)-propenoic acid ethyl ester (Z-isomer)

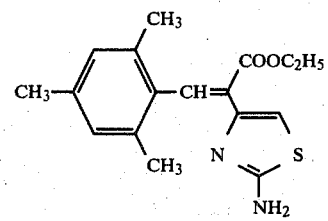

A solution of 32 g of the Z/E mixture prepared in Example 24, 9 g of sodium acetate and 8.8 g of thiourea in 210 ml of tetrahydrofuran and 90 ml of water was stirred at room temperature for 48 hours. The tetrahydrofuran was stripped off and the aqueous phase was adjusted to pH 8 and extracted three times with ethyl acetate. The organic phase was washed with water, dried and evaporated. Crystallization with dioxane gave 8.5 g of the pure Z-isomer, containing ½ mol of dioxane, of melting point 122° to 124°. A second fraction could be obtained from the mother liquor by chromatography.

IR (Nujol): 3600, 3210, 1710, 1640, 1540, 1465, 1285, 1230, 1210, 1140, 1110, 1080, 1040 cm$^{-1}$.

NMR (DMF): δ=7.56 [1] s, 7.30 [2] s, 6.91 [2] s, 6.30 [1] s, 3.99 [2] q, J=7 Hz, 2.23 [3] s, 2.16 [6] s, 0.86 [3] t, J=7 Hz ppm.

Calculated for 1 mol of product+½ mol of dioxane: C 63.2 H 6.7 N 7.8 S 8.9. Found: C 63.0 H 6.8 N 7.7 S 9.0.

EXAMPLE 26

2-(2-Aminothiazol-4-yl)-3-(2,4,6-trimethylphenyl)-propenoic acid (Z-isomer)

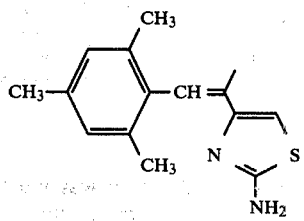

6.1 g of the product from Example 25 were dissolved in a mixture of 150 ml of dioxane and 45 ml of 1.5 N sodium hydroxide solution. The solution was boiled under reflux overnight and the dioxane was then stripped off, the residue was diluted with 50 ml of water and the mixture was filtered. The filtrate was adjusted to pH 5 with dilute hydrochloric acid and was filtered off again after 10 minutes. Recrystallization of the residue from methanol gave the desired product in a yield of 72%.

Melting point: >200°.

IR (KBr): 1675, 1565, 1473, 1393, 1307, 1242, 1199, 1171 cm$^{-1}$.

NMR (DMF): δ=7.52 [1] s, 7.20 [2] s, 6.91 [2] s, 6.75 [1] s, 2.23 [9] s ppm.

Calculated: C 62.5 H 5.6 N 9.7 S 11.1. Found: C 62.0 H 6.0 N 9.8 S 11.2.

EXAMPLE 27

2-(2-Dichlorophosphorylaminothiazol-4-yl)-3-(2,4,6-trimethylphenyl)-propenoic acid chloride (Z-isomer)

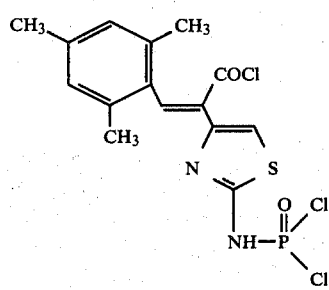

2 g of the carboxylic acid from Example 26 were suspended in 50 ml of emthylene chloride under a nitrogen atmosphere. 3 g of phosphorus pentachloride were added at 0° and the mixture was then stirred at room temperature for 4 hours. After filtration, the filtrate was evaporated and the oil which remained was crystallized with ether. Yield: 1 g. Melting point: 161° to 162° (decomposition).

IR (Nujol): 1760, 1570, 1360, 1310, 1275, 1235, 1175, 1060, 1010, 910 cm$^{-1}$.

NMR (CDCl₃): δ=~14.5–15.5 [1] very broad, 7.82 [1] s, 6.95 [2] s, 6.64 [1] d, J=2 Hz, 2.35 [3] s, 2.30 [6] s ppm.

EXAMPLE 28

(A) Sodium Z-6-[2-(2-aminothiazol-4-yl)-2-(2,4,6-trimethylbenzylidene)-acetamido]-penam-3-carboxylate

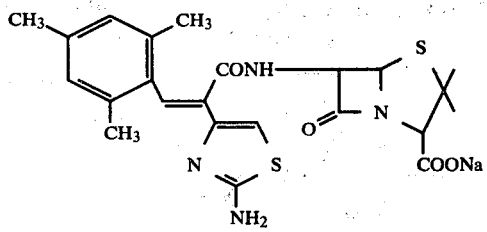

1 g of the product from Example 26 was reacted as described in Example 23. The acid precipitated at pH 2.5 was suspended in ethyl acetate/water and dissolved at pH 7 by adding 2 N sodium hydroxide solution. After the ethyl acetate had been separated off, the aqueous phase was lyophilized. 0.8 g of the sodium salt, which still contained residues of 1-hydroxybenzotriazole, was obtained.

IR (Nujol): 1750, 1600 cm⁻¹.

NMR (CD₃OD): δ=7.44 [1] s, 6.82 [2] s, 6.65 [1] s, 5.45 [1] d, J=5 Hz, 5.37 [1] d, J=5 Hz, 4.07 [1] s, 2.22 [9] s, 1.49 [3] s, 1.43 [3] s.

(B) 0.43 g of 6-aminopenicillanic acid were dissolved in 20 ml of 80 percent strength aqueous tetrahyrofuran at pH 7 to 8 with triethylamine. The product from Example 27 was introduced at 0°, during which the pH was kept at 7.5 by addition of triethylamine. The mixture was subsequently stirred at room temperature for two hours and the tetrahydrofuran was then stripped off and the aqueous solution was extracted twice with ethyl acetate. The aqueous phase was freed from residual ethyl acetate and was then adjusted to pH 2.0 with 2 N hydrochloric acid. The product which had precipitated was filtered off and suspended in 10 ml of water and the suspension was stirred at 50° and at pH 3 for 3 hours. It was filtered again and the residue was converted into the lyophilized sodium salt as described. Yield: 0.7 g.

EXAMPLE 29

Sodium Z-7-[2-(2-aminothiazol-4-yl)-2-(2,4,6-trimethylbenzylidene)-acetamido]-3-acetoxymethyl-3-cephem-4-carboxylate

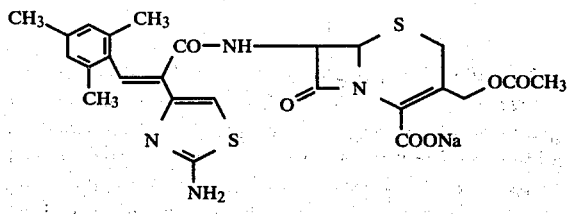

1 g of the product from Example 26 was reacted as described in Example 19. The carboxylic acid precipitated at pH 2.5 was converted into the sodium salt as described in Example 28. Yield: 1.2 g.

IR (Nujol): 1750, 1600, 1520 cm⁻¹.

NMR (CD₃OD): δ=7.35 [1] s, 6.80 [2] s, 6.60 [1] s, 5.59 [1] d, J=5 Hz, 4.99 [1] d, J=12 Hz, 4.93 [1] d, J=5 Hz, 4.81 [1] d, J=12 Hz, 3.50 [1] d, J=17 Hz, 3.21 [1] d, J=17 Hz, 2.24 [6] s, 2.22 [3] s, 2.04 [3] s ppm.

EXAMPLE 30

2-(2-aminothiazol-4-yl)-3-phenylpropenoic acid ethyl ester (Z-isomer)

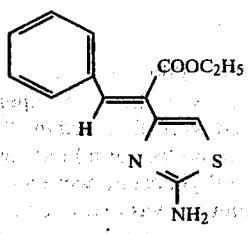

209.2 g of 2-benzylidene-3-oxo-4-chlorobutyric acid ethyl ester (described in J. Amer. Chem. Soc. 66, 1933 (1944)), 63.2 g of thiourea and 104.6 g of sodium acetate were dissolved in a mixture of 1,460 ml of tetrahydrofuran and 630 ml of water. The solution was stirred overnight at room temperature and the tetrahydrofuran was then evaporated off. The aqueous phase was adjusted to pH 8 and extracted three times with ethyl acetate. Drying and evaporation of the organic phase gave a viscous oil, which chiefly consisted of the desired Z-isomer. The product was further processed in the crude form. Yield: 222 g.

IR (CHCl₃): 1710, 1610, 1525, 1380 cm⁻¹.

NMR (CDCl₃): δ=7.46 [1] s, 7.24 [5] s, 6.45 [1] s, 4.18 [2]q, J=7 Hz, 1.10 [3] t, J=7 Hz ppm.

EXAMPLE 31

2-(2-Aminothiazol-4-yl)-3-phenylpropenoic acid (Z-isomer)

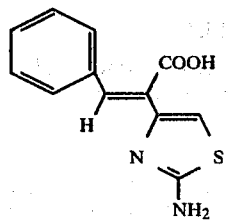

216 g of the crude product from Example 30 were dissolved in a mixture of 1.2 liters of dioxane and 800 ml of 12 percent strength sodium hydroxide solution. The solution was boiled under reflux for 15 hours and the dioxane was then stripped off and the residue was adjusted to pH 8 with 2 N hydrochloric acid. The mixture was extracted three times with ethyl acetate, the aqueous solution was adjusted to pH 3 to 4 and the product which had precipitated was filtered off. 20 g of the desired product of melting point 138° could be obtained directly by recrystallization from methanol. The mother liquor consisted of an E/Z mixture, which could not be separated by crystallization.

IR (KBr): 1650, 1599, 1579, 1564, 1425, 1344, 1304 cm⁻¹.

NMR (CDCl₃+DMSO): δ=7.54 [1] s, 7.32 [5] m, 6.59 [1] s ppm.

EXAMPLE 32

Sodium
Z-6-[2-(2-aminothiazol-4-yl)-2-ben-
zylideneacetamido]penam-3-carboxylate

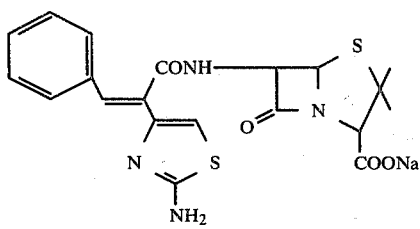

2 g of the product from Example 31 were reacted as described in Example 28 A. 2.6 g of the sodium salt were obtained:

IR (Nujol): 1750, 1600 cm$^{-1}$.

NMR (CD$_3$OD): δ=7.25 [1] s, 7.20 [5] m, 6.50 [1] s, 5.57 [1] d, J=5 Hz, 5.49 [1] d, J=5 Hz, 4.08 [1] s, 1.47 [6] s ppm.

EXAMPLE 33

Sodium
Z-7-[2-(2-aminothiazol-4-yl)-2-benzylideneacetamido]-
3-acetoxymethyl-3-cephem-4-carboxylate

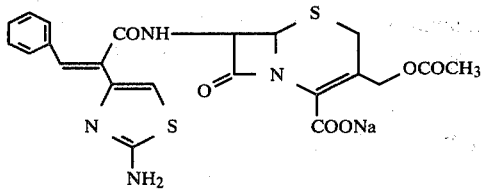

2 g of the product from Example 31 were reacted as described in Example 29. 2.8 g of the sodium salt were obtained.

IR (Nujol): 1755, 1600 cm$^{-1}$.

NMR (CD$_3$OD): δ=7.26 [1] s, 7.20 [5] m, 6.48 [1] s, 5.76 [1] d, J=5 Hz, 5.05 [1] d, J=5 Hz, 4.93 [1] d, J=12.5 Hz, 4.75 [1] d, J=12.5 Hz, 3.52[1] d, J=18 Hz, 3.24 [1] d, J=18 Hz, 1.98 [3] s ppm.

EXAMPLE 34

Sodium
E-6-[2-(2-Aminothiazol-4-yl)-2-(2-
furylidene)acetamido]-penam-3-carboxylate

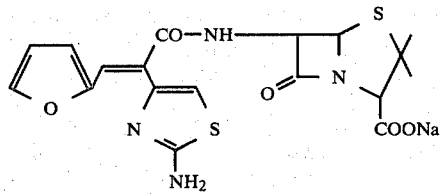

4 g of the product prepared as described in Example 12 were reacted as described in Example 28 A. 3.5 g of the sodium salt were obtained.

IR (Nujol): 1750, 1595 cm$^{-1}$.

NMR (CD$_3$OD): δ=7.62 [1] s, 7.56 [1] s broad, 6.64 [1] s, 6.48 [2] m, 5.62 [2] s, 4.22 [1] s, 1.55 [3] s, 1.53 [3] s ppm.

EXAMPLE 35

2-(2-Aminothiazol-4-yl)-3-(2-furyl)-propenoic acid
ethyl ester (Z-isomer)

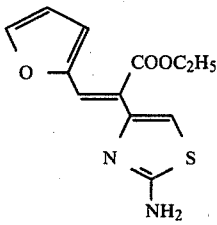

200 g of the isomer mixture prepared as described in Example 10, 68 g of thiourea and 68 g of sodium acetate were dissolved in a mixture of 1 liter of tetrahydrofuran and 250 ml of water. The solution was stirred at room temperature for 24 hours, the tetrahydrofuran was stripped off and the aqueous phase was agitated to pH 8. The aqueous phase was extracted three times with ethyl acetate and the combined ethyl acetate phases were washed once with water, dried over magnesium sulphate and concentrated, whereupon a small amount of the E-isomer (4.7 g) could be crystallized. The mother liquor was evaporated completely and the oil which remained was crystallized with ethanol. 106 g of the pure Z-isomer of melting point 109° to 110° were obtained.

IR (Nujol): 1700, 1635, 1590, 1520, 1350, 1230, 1190, 1140, 1020 cm$^{-1}$.

NMR (DMF): δ=7.65 [1] m, 7.18 [3] s broadened, 6.50 [3] m, 4.35 [2] q, J=7 Hz, 1.30 [3] t, J=7 Hz ppm.

Calculated: C 54.5 H 4.6 N 10.6 S 12.1. Found: C 53.9 H 4.6 N 10.5 S 11.2.

EXAMPLE 36

2-(2-Aminothiazol-4-yl)-3-(2-furyl)-propenoic acid
(Z-isomer)

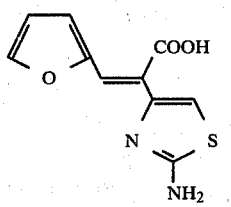

300 ml of 2 N sodium hydroxide solution were added to a solution of 61 g of the product prepared according to Example 35 in 1 liter of dioxane and the mixture was boiled under reflux for 7 hours. The dioxane was stripped off and the aqueous solution was adjusted to pH 9 with 2 N hydrochloric acid and extracted three times with ethyl acetate. The product phase was then adjusted to pH 2.0 and filtered. Recrystallization of the residue from ethanol gave 41 g of the product of melting point 143° (decomposition).

IR (KBr): 1660, 1635, 1612, 1575, 1468, 1421, 1308 cm$^{-1}$.

NMR (DMSO): δ=7.62 [1] d, J=2 Hz, 6.91 [1] s, 6.53 [2]m, 6.42 [1] s ppm.

EXAMPLE 37

2-(2-Aminothiazol-4-yl)-3-(2-furyl)-propenoic acid chloride hydrochloride (Z-isomer)

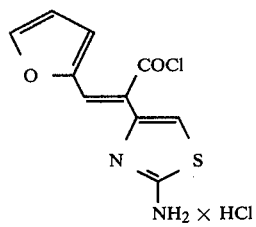

10 g of the dried product prepared according to Example 36 were suspended in 120 ml of absolute methylene chloride under a nitrogen atmosphere. 17.5 g of phosphorus pentachloride were added at 0° and the mixture was allowed to come to room temperature and was subsequently stirred for 4.5 hours. The product was filtered off, yield: 6.3 g, melting point: 123° (decomposition).

IR (Nujol): 1779, 1622, 1295 cm$^{-1}$.

NMR (DMF): δ=12.7 [3] s very broad, 7.83 [1] d, J=2 Hz, 7.46 [1] s, 6.96 [1] s, 6.91 [1] d, J=4 Hz, 6.64 [1] dd, J=2 Hz, J=4 Hz ppm.

MS: 192, 150

EXAMPLE 38

Sodium Z-7-[2-(2-aminothiazol-4-yl)-2-(2-furylidene)-acetamido]-3-acetoxymethyl-3-cephem-4-carboxylate

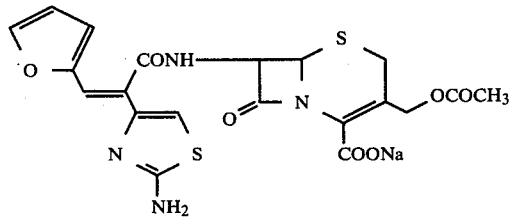

1 g of the product from Example 37 was added to a solution of 0.8 g of 7-aminocephalosporanic acid and 1.3 ml of triethylamine in 100 ml of absolute methylene chloride at 0°. The mixture was subsequently stirred at 0° for 30 minutes and at room temperature for 4 hours and was then poured onto water and adjusted to pH 6.5. After the organic solvent had been stripped off, the aqueous phase was extracted three times with ethyl acetate and then adjusted to pH 2.5. The mixture was filtered and the residue was converted into the sodium salt as described in Example 28. Yield: 1.1 g.

IR (Nujol): 1750, 1600, 1520, 1325, 1232, 1020 cm$^{-1}$.

NMR (CD$_3$OD): δ=7.60 [1] d, J=1.5 Hz, 7.15 [1] s, 6.61 [1] d, J=4 Hz, 6.56 [1] s, 6.51 [1]dd, J=4 Hz, J=1.5 Hz, 5.98 [1] d, J=5 Hz, 5.21 [1] d, J=5 Hz, 5.05 [1] d, J=13 Hz, 4.88 [1] d, J=13 Hz, 3.66 [1] d, J=18 Hz, 3.38 [1] d, J=18 Hz, 2.07 [3] s ppm.

EXAMPLE 39

Sodium Z-6-[2-(2-aminothiazol-4-yl)-2-(2-furylidene)-acetamido]-penam-4-carboxylate

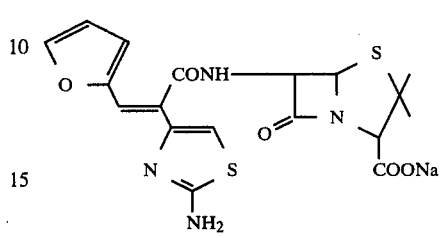

2 g of the acid chloride from Example 37 were reacted with 1.5 g of 6-aminopenicillanic acid analogously to Example 38. 2.4 g of the sodium salt were obtained.

IR (Nujol): 3300, 1750, 1600, 1510, 1310 cm$^{-1}$.

NMR (CD$_3$OD): δ=7.57 [1] d, J=2 Hz, 7.13 [1] s, 6.56 [1] s, 6.56 [1] d, J=3 Hz, 6.49 [1] dd, J=2 Hz, J=3 Hz, 5.79 [1] d, J=5 Hz, 5.69 [1] d, J=5 Hz, 4.24 [1] s, 1.26 [3] s, 1.22 [3] s ppm.

EXAMPLE 40

2-(2-Dichlorophosphorylaminothiazol-4-yl)-3-(2,6-dichlorophenyl)-propenoic acid chloride (Z-isomer)

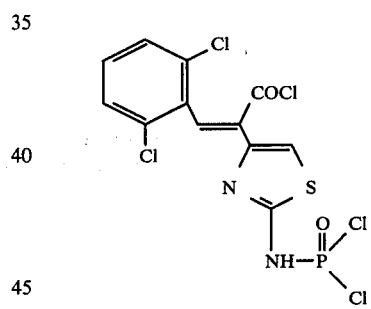

26.2 g of phosphorus pentachloride were introduced in portions into a suspension of 20 g of the product prepared as described in Example 6 in 200 ml of absolute methylene chloride at 0° under a nitrogen atmosphere. The mixture was subsequently stirred until a clear solution had formed, and this solution was then evaporated. The residue was stirred with ether and the product was filtered off, washed thoroughly with ether and recrystallized from acetonitrile.

Yield: 10 g, melting point: 174° to 176° (decomposition).

IR (Nujol): 1760, 1570, 1545, 1235, 1000 cm$^{-1}$.

NMR (acetone-d$_6$): δ=7.80 [1] s, 7.58 [3] s, 7.43 [1] d, J=2 Hz ppm.

MS: 448, 413, 377, 117, 82, 66, 47, 36.

Calculated: C 32.0 H 1.3 N 6.2 S 7.1 Cl 39.4 P 6.9.
Found: C 32.1 H 1.7 N 5.8 S 7.4 Cl 39.2 P 7.2.

EXAMPLE 41

Z-6-[2-(2-Dihydroxyphosphorylaminothiazol-4-yl)-2-(2,6-dichlorobenzylidene)-acetamido]-penam-3-carboxylic acid

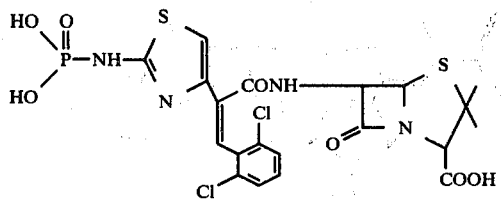

3 g of 6-aminopenicillanic acid were dissolved in 100 ml of 80 percent strength aqueous tetrahydrofuran with one equivalent of triethylamine. The solution was cooled to 0° and 5 g of the product from Example 40 were introduced, during which the pH of the solution was kept at 7.5 by addition of triethylamine. The mixture was subsequently stirred for 30 minutes and the tetrahydrofuran was then stripped off and the aqueous solution was adjusted to pH 1.8 with 2 N hydrochloric acid. The solution was stirred at this pH for one hour and was then adjusted to pH 6.5 with 2 N sodium hydroxide solution and extracted three times with ethyl acetate. The aqueous phase was adjusted to pH 1.8 again and the product was filtered off, washed with water and dried. It contained one mole of triethylamine. Yield: 7.5 g.

IR (Nujol): 1775, 1740, 1665, 1570, 1550, 1495, 1290, 1080 cm$^{-1}$.

NMR (CD$_3$OD/DMF): δ=7.50 [4] m, 7.25 [1] s, 5.71 [1] d, J=4 Hz, 5.62 [1] d, J=4 Hz, 4.45 [1] s, 1.65 [3] s, 1.58 [3] s ppm.

EXAMPLE 42

Sodium Z-6-[2-(2-aminothiazol-4-yl)-2-(2,6-dichlorobenzylidene)-acetamido]-penam-3-carboxylate

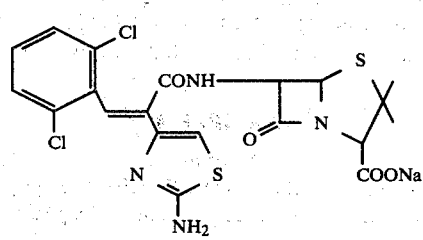

A suspension of 4 g of the product from Example 41 in 20 ml of water was warmed to 50° at pH 3 for 3 hours, with stirring. The mixture was filtered and the residue was washed with water and converted into the sodium salt as described in Example 28. Yield: 2.4 g.

IR (Nujol): 1755, 1600, 1500, 1300, 1090 cm$^{-1}$

NMR (CD$_3$OD): δ=7.45 [3] m, 7.36 [1] s, 6.85 [1] s, 5.55 [1] d, J=4 Hz, 5.51 [1] d, J=4 Hz, 4.20 [1] s, 1.40 [3] s, 1.38 [3] s ppm.

EXAMPLE 43

2-(2-Trifluoromethylbenzylidene)-3-oxo-4-chlorobutyric acid ethyl ester

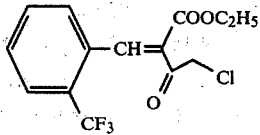

226.2 g of 2-trifluoromethylbenzaldehyde, 235 g of 4-chloroacetoacetic acid ethyl ester, 4.2 ml of glacial acetic acid and 2.1 ml of piperidine were dissolved in 500 ml of benzene and the solution was boiled for 8 hours using a water separator. 1 liter of ethyl acetate was added and the mixture was extracted twice with sodium bicarbonate, once with citric acid and once more with water, dried and evaporated. The crude product was subjected to incipient distillation up to 130° under a high vacuum and the product remained as the residue in the form of a chromatographically pure 2:1 isomer mixture.

Yield: 234 g.

IR (film): 1720, 1620, 1575, 1490, 1450, 1400, 1375, 1320, 1300, 1260, 1175, 1130, 1062, 1040 cm$^{-1}$.

NMR (CDCl$_3$): δ=8.20 [1] m, 7.3–7.8 [4] m, 4.59/4.40 [2] s, 4.38/4.10 [2] q, J=7 Hz, 1.32/1.00 [3] t, J=7 Hz ppm.

Calculated: C 52.4 H 3.8 Cl 11.1 F 17.8. Found: C 51.5 H 3.7 Cl 11.3 F 17.3.

EXAMPLE 44

2-(2-Aminothiazol-4-yl)-3-(2-trifluoromethylphenyl)-propenoic acid ethyl ester

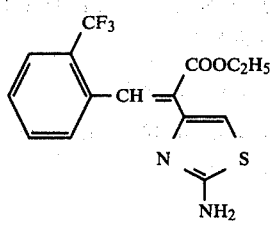

A solution of 234 g of the product from Example 43 and 55.5 g of thiourea in 500 ml of ethanol was stirred at 50° for 3 hours and was then evaporated. The residue was taken up in water/ethyl acetate, the mixture was adjusted to pH 8 and the aqueous phase was extracted three times with ethyl acetate. The combined ethyl acetate extracts were washed once with water, dried over magnesium sulphate and concentrated to about 300 ml. After the concentrate had been left to stand overnight, it was filtered and the residue was washed with ether. 44.8 g of the E-isomer were thus obtained. Melting point: 145° to 147°.

68 g of the pure Z-isomer could be obtained from the evaporated mother liquor by fractional crystallization of the residue from toluene. Melting point: 97° to 98°.

E-isomer:

IR (Nujol): 3350, 1690, 1635, 1625, 1520, 1310, 1260, 1150, 1120, 1035 cm$^{-1}$.

NMR (CDCl$_3$): δ=8.0 [1] m, 7.0–7.8 [4] m, 6.16 [1] s, 5.24 [2] s, broad, 4.30 [2] q, J=7 Hz, 1.30 [3] t, J=7 Hz ppm.

Calculated: C 52.6 H 3.8 N 8.2 S 9.4 F 16.6. Found: C 51.6 H 3.9 N 7.9 S 9.3 F 16.7.

Z-isomer:

IR (Nujol): 3350, 3220, 3100, 1700, 1623, 1530, 1350, 1310, 1260, 1230, 1170, 1110, 1060, 1025 cm$^{-1}$.

NMR (DMSO): δ=7.3-7.9 [5] m, 7.23 [2] s, broad, 6.65 [1] s, 4.06 [2] q, J=7 Hz, 0.95 [3] t, J=7 Hz ppm.

Calculated: C 52.6 H 3.8 N 8.2 S 9.4 F 16.6. Found: C 52.1 H 4.1 N 7.9 S 9.5 F 17.2.

EXAMPLE 45

2-(2-Aminothiazol-4-yl)-3-(2-trifluoromethylphenyl)-propenoic acid (E-isomer)

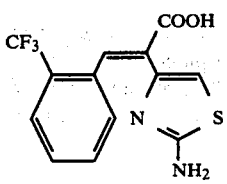

44 g of the E-isomer prepared as described in Example 44 were reacted as described in Example 15. The product was recrystallized from methanol. Yield: 33.5 g, melting point: 222° to 223° (decomposition).

IR (Nujol): 1650 (shoulder), 1620, 1590, 1520, 1315, 1180, 1120, 1095, 1060, 1030 cm$^{-1}$.

NMR (DMSO): δ=7.1-8.0[5]m, 7.06 [2]s broad, 6.23 [1] s ppm.

Calculated: C 49.7 H 2.9 N 8.9 S 10.2 F 18.1. Found: C 49.1 H 3.2 N 8.9 S 10.0 F 18.3.

EXAMPLE 46

2-(2-Aminothiazol-4-yl)-3-(2-trifluoromethylphenyl)-propenoic acid (Z-isomer)

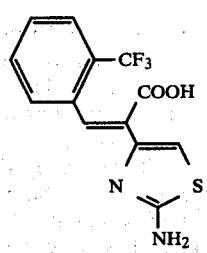

66.5 g of the Z-isomer prepared as described in Example 44 were reacted as described in Example 36. Recrystallization from methanol gave 43.4 g of the product of melting point 205° to 207° (decomposition).

IR (Nujol): 1625, 1400, 1310, 1260, 1170, 1108 cm$^{-1}$.

NMR (DMSO): δ=7.3-7.8 [4] m, 7.53 [1] s, 7.14 [2] s broad, 6.57 [1] s ppm.

Calculated: C 49.7 H 2.9 N 8.9 S 10.2 F 18.1. Found: C 49.5 H 3.5 N 8.6 S 10.0 F 18.2.

EXAMPLE 47

Z-6-[2-(2-Aminothiazol-4-yl)-2-(2-trifluoromethylbenzylidene) acetamido]penam-3-carboxylic acid

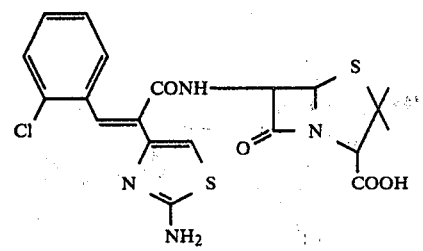

4.7 g of the product prepared as described in Example 46 were reacted as described in Example 23 and 4.2 g of product were obtained.

IR (Nujol): 1750, 1715, 1650, 1600, 1310 cm$^{-1}$.

NMR (CD$_3$OD): δ=7.3-7.8 [5] m, 6.67 [1] s, 5.56 [1] d, J=4 Hz, 5.48 [1] d, J=4 Hz, 4.16 [1] s, 1.50 [3] s, 1.47 [3] s ppm.

EXAMPLE 48

Sodium Z-7-[2-(2-aminothiazol-4-yl)-2-(2-trifluoromethylbenzylidene)-acetamido]-3-acetoxymethyl-3-cephem-4-carboxylate

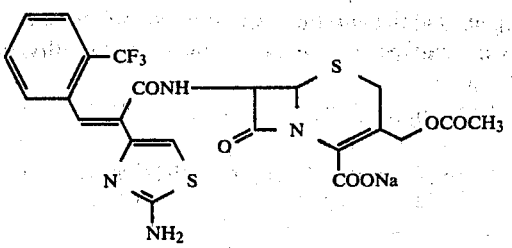

4.7 g of the product from Example 46 were reacted as described in Example 29 and 5.2 g of the sodium salt were obtained.

IR (Nujol):1750, 1600, 1520, 1310 cm$^{-1}$.

NMR (CD$_3$OD): δ=7.7 [3] m, 7.53 [1] t, J=6 Hz, 7.41 [1] t, J=6 Hz, 6.65 [1] s, 5.74 [1] d, J=4 Hz, 5.02 [1] d, J=4 Hz, 4.99 [1] d, J=12 Hz, 4.85 [1] d, J=12 Hz, 3.52 [1] d, J=18 Hz, 3.26 [1] d, J=18 Hz, 2.00 [3] s, ppm.

EXAMPLE 49

Sodium E-7-[2-(2-aminothiazol-4-yl)-2-(2-trifluoromethylbenzylidene)acetamido]-3-acetoxymethyl-3-cephem-4-carboxylate

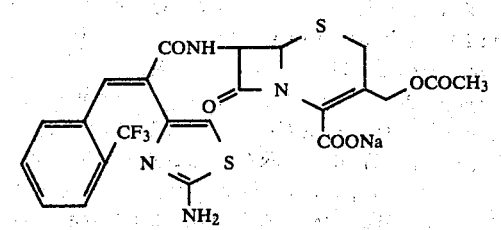

4.7 g of the product prepared as described in Example 45 were reacted as described in Example 29 and 4.5 g of the sodium salt were obtained.

IR (Nujol): 1750, 1600, 1310, 1100 cm$^{-1}$.

NMR (CD$_3$OD): δ=7.95 [1] s, 7.68 [1] m, 7.40 [2] m, 7.18 [1] m, 5.91 [1] s, 5.87 [1] d, J=4 Hz, 5.11 [1] d, J=4 Hz, 5.03 [1] d, J=12 Hz, 4.87 [1] d, J=12 Hz, 3.60 [1] d, J=17 Hz, 3.35 [1] d, J=17 Hz, 2.02 [3] s ppm.

EXAMPLE 50

2-(2,3,6-Trichlorobenzylidene)-3-oxo-4-chlorobutyric acid ethyl ester

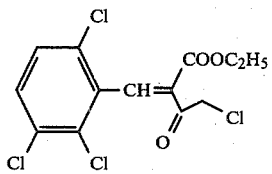

210 g of 2,3,6-trichlorobenzaldehyde were reacted with 4-chloroacetoacetic acid ethyl ester as described in Example 43. 213 g of a 3:1 isomer mixture were obtained as an oily crude product.

NMR (DMSO): δ=7.5-8.0 [3] m, 5.02/4.80 [2] s, 4.10/4.30 [2] q, J=7 Hz, 1.33/0.96 [3] t, J=7 Hz ppm.

EXAMPLE 51

2-(2-Aminothiazol-4-yl)-3-(2,3,6-trichlorophenyl)-propenoic acid ethyl ester hydrochloride

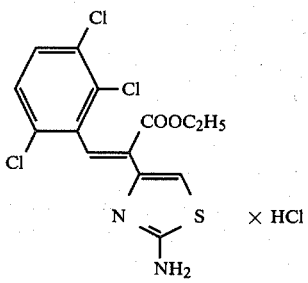

213 g of the product from Example 50 and 30 g of thiourea, dissolved in 500 ml of ethanol, were stirred at 15° for 15 hours. The mixture was evaporated and the residue was crystallized with acetone. After recrystallization of the product from acetone, 35 g of the Z-isomer of melting point 178° were obtained.

Evaporation of the mother liquor gave 166 g of the E/Z mixture as a viscous oil which, after being converted into the free base, could be separated by chromatography (mobile phase: methylene chloride/methanol=95/5).

Z-isomer: (hydrochloride)

IR (Nujol): 1700, 1620, 1550, 1295, 1235, 1175, 1140, 1030 cm$^{-1}$.

NMR (DMSO): δ=9.10 [3] s broad, 7.71 [1] s, 7.76 [1] d, J=9 Hz, 7.60 [1] d, J=9 Hz, 7.20 [1] s, 4.05 [2] q, J=7 Hz, 0.90 [3] t, J=7 Hz ppm.

Calculated: C 40.6 H 2.9 N 6.8 S 7.7 Cl 34.2 . Found: C 40.7 H 2.9 N 6.6 S 7.5 Cl 33.0.

E-isomer: (free base)
Melting point: 172°.
IR (Nujol): 1690, 1625, 1525, 1275, 1245 cm$^{-1}$.

NMR (DMSO): δ=7.62 [1] d, J=9 Hz, 7.48 [1] d, J=9 Hz, 7.26 [1] S, 6.72 [2] s broad, 6.48 [1] s, 4.28 [2] q, J=7 Hz, 1.30 [3] t, J=7 Hz ppm.

EXAMPLE 52

2-(2-Aminothiazol-4-yl)-3-(2,3,6-trichlorophenyl)-propenoic acid (Z-isomer)

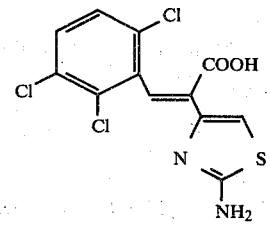

25 g of the Z-isomer from Example 51 and 100 ml of 2 N NaOH, dissolved in 500 ml of dioxane, were boiled under reflux for 5 hours. Working up according to Example 36 gave 18.5 g of product of melting point: >210°.

IR (Nujol): 1600, 1565, 1300, 1225, 1170, 1090 cm$^{-1}$.

NMR (DMSO): δ=7.63 [1] d, J=9 Hz, 7.50 [1] d, J=9 Hz, 7.46 [1] s, 6.92 [1] s ppm.

EXAMPLE 53

2-(2-Dichlorophosphorylaminothiazol-4-yl)-3-(2,3,6-trichlorophenyl)propenoic acid chloride (Z-isomer)

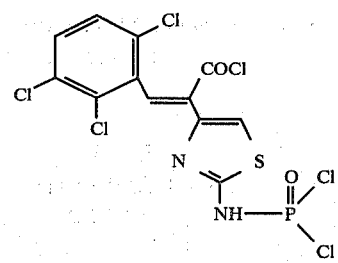

3.5 g of the product from Example 52 were reacted as described in Example 40. 2.8 g of crystalline product of melting point 200° (decomposition) were obtained from ether.

NMR (CDCl$_3$): δ=7.70 [1] s, 7.53 [1] s, 7.48 [1] s, 7.36 [1] s, 6.98 [1] d, J=2 Hz ppm.

EXAMPLE 54

2-(2-Aminothiazol-4-yl)-3-(2,6-dichlorophenyl)-propenoic acid chloride hydrochloric (Z-isomer)

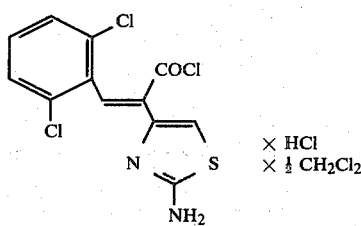

30 μl of water were added to a suspension of 1 g of the product from Example 6 in 30 ml of methylene chloride, and 1.3 of phosphorus pentachloride were then added at 0°. The mixture was stirred at room temperature for 3 hours and the product was then filtered off, washed with methylene chloride and dried. Yield: 1.1 g, melting point: 234° (decomposition).

IR (Nujol): 3210, 1760, 1630, 1570, 1550, 1300, 1255, 1195, 1180, 1090, 1030 cm$^{-1}$.

NMR (THF-D$_8$): δ=7.86 [1] s, 7.36 [3] m, 6.85 [1] s ppm.

Calculated: C 36.3 H 2.2 N 6.8 S 7.7 Cl 43.0. Found: C 35.9 H 2.0 N 6.7 S 7.7 CL 41.1.

EXAMPLE 55

Sodium Z-7-[2-(2-aminothiazol-4-yl)-2-(2,3,6-trichlorobenzylidene)acetamido]-3-acetoxymethyl-3-cephem-4-carboxylate

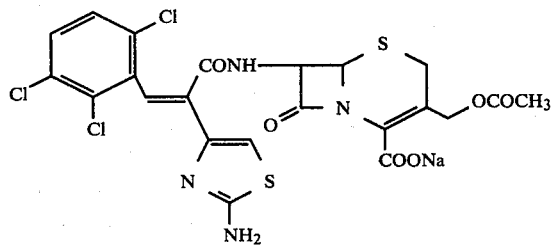

4 g of the product from Example 52 were reacted as described in Example 29 and 6 g of the sodium salt were obtained.

IR (Nujol): 1755, 1650, 1600, 1510, 1230 cm$^{-1}$.

NMR (CD$_3$OD): δ=7.44 [1] d, J=8 Hz, 7.36 [1] d, J=8 Hz, 7.24 [1] s, 6.76 [1] s, 5.65 [1] d, J=5 Hz, 4.98 [1] d, J=12 Hz, 4.96 [1] d, J=5 Hz, 4.80 [1] d, J=12 Hz, 3.53 [1] d, J=18 Hz, 3.25 [1] d, J=18 Hz, 2.02 [3] s ppm.

EXAMPLE 56

Sodium Z-6-[2-(2-aminothiazol-4-yl)-2-(2,3,6-trichlorobenzylidene)acetamido]penam-4-carboxylate

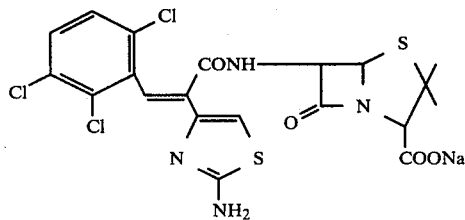

4 g of the product from Example 52 were reacted as described in Example 28 and 3.3 g of the sodium salt were obtained.

IR (NUjol): 1750, 1600, 1190, 1170, 1095 cm$^{-1}$.

NMR (CD$_3$OD): δ=7.45 [1] d, J=8 Hz, 7.37 [1] d, J=8 Hz, 7.28 [1] s, 6.79 [1] s, 5.47 [2] m, 4.15 [1] s, 1.55 [3] s, 1.51 [3] s ppm.

EXAMPLE 57

2-(2-tert.-Butoxycarbonylaminothiazol-4-yl)-4-oxo-2-pentenoic acid ethyl ester

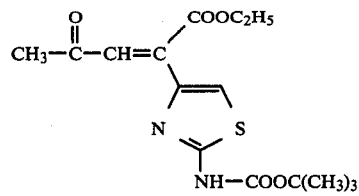

3.5 g of sodium hydride were suspended in 100 ml of absolute dimethoxyethane (DME) in a thoroughly heated flask under nitrogen. 20 g of diethyl-2-oxopropylphosphonate, dissolved in 100 ml of DME, were added dropwise at room temperature. The mixture was subsequently stirred for one hour and a solution of 30 g of 2-(2-tert.-butoxycarbonylaminothiazol-4-yl)-glyoxylic acid ethyl ester in 100 ml of DME was then added dropwise. After the mixture had been stirred overnight, hydrolysis was carried out with ice and 1 N citric acid solution and the mixture was adjusted to pH 6. The DME was stripped off and the aqueous phase was extracted three times with ethyl acetate. The combined ethyl acetate phases were dried and concentrated. The oil which remained was crystallized with ether/petroleum ether and this crude product (yield: 62%, melting point: 107° to 108°) was recrystallized from cyclohexane. Yield: 44%, melting point: 108° to 110°. A pure isomer is obtained.

IR (KBr): 3284 (broad), 3085, 1717, 1700 (shoulder), 1686, 1591, 1550, 1246, 1150 cm$^{-1}$.

NMR (CDCl$_3$): δ=7.10 [1] s, 6.96 [1] s, 4.42 [2] q, J=7 Hz, 2.28 [3] s, 1.54 [9] s, 1.38 [3] t, J=7 Hz ppm.

Calcluted: C 52.9 H 5.9 N 8.2 S 9.4. Found: C 52. 1 H 5.9 N 7.4 S 8.5.

EXAMPLE 58

2-(2-tert.Butoxycarbonylaminothiazol-4-yl)-4-hydroxy-4-methylbutenolide

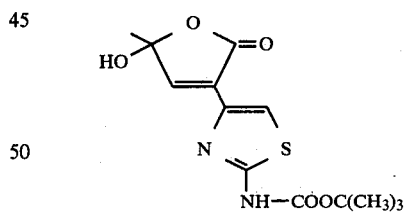

A suspension of 15 g of the product prepared in Example 57 in a mixture of 100 ml of methanol and 20 ml of water was adjusted to pH 13 with 2 N sodium hydroxide solution and was stirred at room temperature until the pH remained constant (2 to 3 hours). The pH was adjusted to 7, the methanol was stripped off, the mixture was filtered and the filtrate was washed twice with ethyl acetate. The aqueous phase was then adjusted to pH 1.8 and extracted three times with ethyl acetate. The combined ethyl acetate phases were dried and evaporated and the product was obtained as a yellow hard foam.

Yield: 88%.

IR (KBr): 3399, 1769, 1727, 1543, 1443, 1371, 1208, 1154 cm$^{-1}$.

NMR (CDCl₃): δ=7.70 [1] s, 7.35 [1] s, 6.80 [2] s very broad, 1.76 [3] s, 1.57 [9] s ppm.

MS: 312, 256, 212, 197, 195, 169, 151, 125, 57.

Calculated: C 50.0 H 5.2 N 9.0 S 10.3. Found: C 49.2 H 5.3 N 8.5 S 9.9.

EXAMPLE 59

Triethylammonium 2-(2-tert.-butoxycarbonylaminothiazol-4-yl)-3-oxo-pentenoate

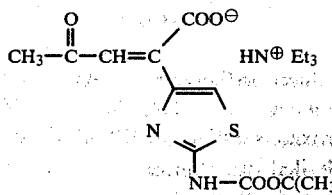

The product prepared in Example 58 was dissolved in ethyl acetate, and water was added to the solution. The pH was adjusted to 7 with triethylamine, the ethyl acetate was separated off and the aqueous phase was lyophilised.

IR (KBr): 1608, 1527, 1370, 1239 (all broad), 1140 cm⁻¹.

NMR (D₂O): δ=7.34 [1] s, 6.77 [1] s, 3.21 [6] q, J=7 Hz, 2.33 [3] s, 1.52 [9] s, 1.29 [9] t, J=7 Hz ppm.

EXAMPLE 60

2-(2-tert.-Butoxycarbonylaminothiazol-4-yl)-4-methoxyimino-2-pentenoic acid

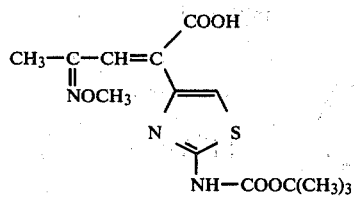

A solution of 12.75 g of the product from Example 58, 3.6 g of hydroxylamine methyl ether hydrochloride and 12.5 ml of triethylamine in 150 ml of ethanol was stirred at room temperature for 24 hours. The ethanol was stripped off, the residue was taken up in ethyl acetate and the mixture was extracted three times with 2 N hydrochloric acid and once with water. After the mixture had been dried and evaporated, the oil which remained was crystallised from acetonitrile or carbon tetrachloride.

Yield: 7.7 g, melting point: 165° (decomposition).

IR (Nujol): 3150, 1700, 1550, 1300, 1250, 1180, 1155, 1080, 1055 cm⁻¹.

NMR (DMSO): δ=7.08 [1] s, 6.83 [1] s, 3.87 [3] s, 1.98 [3] s, 1.50 [9] s ppm.

MS: 341, 295, 285, 241, 222

Calculated (x1/3CCl₄): C 43.8 H 4.8 N 10.7 S 8.1. Found: C 44.3 H 5.1 N 10.4 S 8.0.

EXAMPLE 61 tert.-Butyl-7-[2-(2-tert.-butoxycarbonylaminothiazol-4-yl)-4-methoxyimino-pent-2-enoyl]amino-3-acetoxymethyl-3-cephem-4-carboxylate

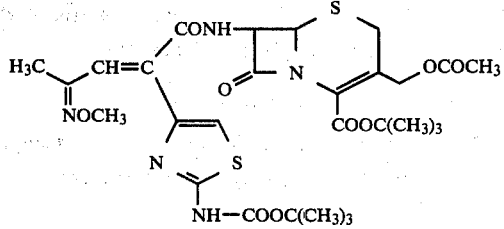

0.4 g of 1-hydroxybenzotriazole and 0.6 g of dicyclohexylcarbodiimide were added to a solution of 1 g of the product from Example 60 in 30 ml of absolute tetrahydrofuran. The mixture was stirred at room temperature for 5 hours, a solution of 1 g of 7-aminocephalosporanic acid tert.-butyl ester in 20 ml of tetrahydrofuran was then added and the mixture was stirred overnight at room temperature. The dicyclohexylurea was filtered off, the filtrate was evaporated and the residue was dissolved in ethyl acetate. The solution was extracted three times with sodium bicarbonate solution and once with water, dried and evaporated. Titration of the residue with ether, filtration of the mixture and evaporation of the filtrate gave 1.2 g of a crude product which was purified by chromatography on silica gel (mobile phase: toluene/ethyl acetate 4:1). Yield: 320 mg.

IR (KBr): 3284, 2979, 2932, 1787, 1725, 1679, 1551, 1453, 1370, 1245, 1154, 1105, 1052 cm⁻¹.

NMR (CDCl₃): δ=8.70 [1] s broad, 7.46 [1] d, J=9 Hz, 7.20 [1] s, 7.03 [1] s, 5.89 [1] dd, J=9 Hz, J=5 Hz, 5.10 [1] d, J=13 Hz, 5.01 [1] d, J=5 Hz, 4.79 [1] d, J=13 Hz, 3.88 [3] s, 3.55 [1] d, J=18 Hz, 3.36 [1] d, J=18 Hz, 2.08 [3] s, 2.07 [3] s, 1.52 [18] s ppm.

EXAMPLE 62

2-(2,4,5-Trimethoxybenzylidene)-3-oxo-4-chlorobutyric acid ethyl ester

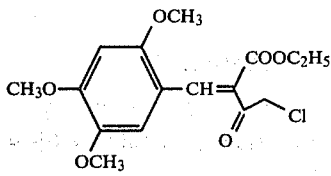

42 g of 4-chloroacetoacetic acid ethyl ester, 50 g of 2,4,5-trimethoxybenzaldehyde, 2.5 ml of glacial acetic acid and 1 ml of piperidine were dissolved in 60 ml of benzene and the solution was boiled for two hours using a water separator. Although conversion was not yet complete, the mixture was worked up. It was diluted with 200 ml of ethyl acetate, extracted in each case three times with saturated sodium bicarbonate solution, water, 1 M citric acid solution and again with water, dried and evaporated. On fractional crystallization of the residue from methanol, first 20 g of pure product, as the E/Z mixture, and then 10.5 g of unreacted aldehyde could be crystallized. In addition to a large amount of product, the mother liquor still contained only a little aldehyde and, after preliminary purification by chromatography on silica gel, could likewise be crystallized. A further 25 g of product were obtained.

IR (Nujol): 1715, 1680, 1595, 1505, 1405, 1370, 1340, 1270, 1210, 1165, 1120, 1020 cm$^{-1}$.

NMR (CDCl$_3$): δ=8.09 [1] s, 7.00/6.80 [1] s, 6.71 [1] s, 4.50/4.41 [2] s, 4.33 [2] q, J=7 Hz, 3.98 [3] s, 3.88 [3] s, 3.83 [3] s, 1.36/1.32 [3] t, J=7 Hz ppm.

EXAMPLE 63

2-(2-Aminothiazol-4-yl)-3-(2,4,5-trimethoxyphenyl)-propenoic acid ethyl ester (Z-isomer)

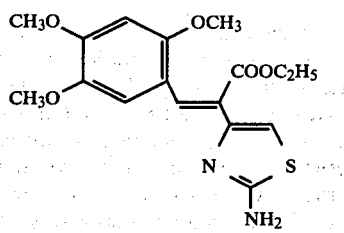

54.8 g of the E/Z mixture from Example 62 were reacted according to Example 25. After the tetrahydrofuran had been stripped off and the aqueous phase had been adjusted to pH 8, some of the pure Z-isomer crystallized and was recrystallized from acetone, giving a yield of 12.5 g with a melting point of 194°. Extraction of the aqueous phase with ethyl acetate and drying and evaporation of the organic phase gave 44 g of the E/Z mixture as a dark-colored oil.

IR (Nujol): 3320, 1700, 1635, 1600, 1510, 1395, 1320, 1290, 1270, 1230, 1200, 1150, 1110, 1025 cm$^{-1}$.

NMR (DMSO): δ=7.62 [1] s, 7.22 [2] s, broadened, 6.91 [1] s, 6.82 [1] s, 6.51 [1] s, 4.33 [2] q, J=7 Hz, 3.93 [6] s, 3.78 [3] s, 1.25 [3] t, J=7 Hz ppm.

Calculated: C 55.9 H 5.8 N 7.7 S 8.8. Found: C 55.7 H 5.8 N 7.5 S 8.8.

EXAMPLE 64

2-(2-Aminothiazol-4-yl)-3-(2,4,5-trimethoxyphenyl)-propenoic acid ethyl ester hydrochloride (E-isomer)

5 g of the E/Z mixture from Example 62 and 1.1 g of thiourea were stirred in 100 ml of ethanol at room temperature overnight and the mixture was then warmed to 50° for 6 hours. After the mixture had been cooled, the product was filtered off, and a second fraction of the same purity could be obtained by concentration of the mother liquor and renewed filtration. Yield: 4.4 g melting point: 200° (decomposition).

IR (Nujol): 3220, 1680, 1625, 1595, 1575, 1490, 1400, 1340, 1285, 1255, 1210, 1120, 1040 cm$^{-1}$.

NMR (DMSO): δ=8.17 [1] s, 6.75 [2] s, 6.60 [1] s, 4.23 [2] q, J=7 Hz, 3.90 [6] s, 3.53 [3] s, 1.25 [3] t, J=7 Hz ppm.

EXAMPLE 65

2-(2-Aminothiazol-4-yl)-3-(2,4,5-trimethoxyphenyl)-propenoic acid

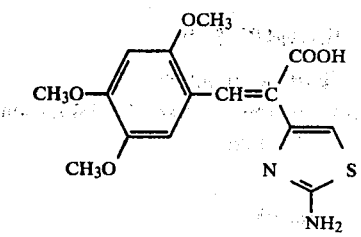

5.5 g of the product for Example 63 were suspended in 200 ml of dioxane and, after the addition of 24 ml of 2 N sodium hydroxide solution and 10 ml of water, the suspension was boiled under reflux for 12 hours. The dioxane was stripped off and the aqueous phase was extracted twice with ethyl acetate and adjusted to pH 2.5. The product was filtered off and dried. Yield: 3.4 g of an E/Z mixture.

IR (Nujol): 1650, 1600, 1495, 1330, 1290, 1260, 1206, 1120, 1020 cm$^{-1}$.

E-isomer

NMR (DMSO): δ=7.90 [1] s, 6.86 [2] s broadened, 6.62 [1] s, 6.58 [1] s, 6.30 [1] s, 3.82 [3] s, 3.80 [3] s, 3.43 [3] s ppm.

Z-isomer

NMR (DMSO): δ=7.39 [1] s, 6.98 [2] s broadened, 6.66 [1] s, 6.55 [1] s, 6.34 [1] s, 3.80 [6] s, 3.63 [3] s ppm.

EXAMPLE 66

2-(4-Hydroxybenzylidene)-3-oxo-4-chlorobutyric acid ethyl ester

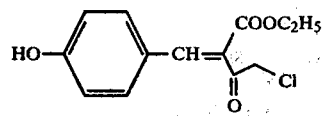

122 g of 4-hydroxybenzaldehyde were reacted, and the mixture was worked up, as described in Example 24. After unreacted 4-chloroacetoacetic acid ethyl ester had been distilled off, the crude product was left to stand overnight in order to crystallize. It was stirred with a mixture of 200 ml of toluene and 50 ml of cyclohexane, and 21 g of p-hydroxybenzaldehyde were filtered off. The mother liquor was evaporated again and the residue was left to stand for several days to crystallize. After treatment with toluene, 85 g of an E/Z mixture of melting point 92° to 95° were obtained.

IR (Nujol): 3310, 1700, 1665, 1660, 1570, 1505, 1400, 1310, 1285, 1210, 1160, 1010 cm$^{-1}$.

NMR (DMSO): δ=10.40 [1] s broad, 7.76/7.72 [1] s, 7.45/7.33 [2] d, J=7 Hz, 6.91/6.88 [1] d, J=7 Hz, 4.96/4.68 [2] s, 4.32/4.23 [2] q, J=7 Hz, 1.25 [3] t, J=7 Hz ppm.

Calculated: C 58.1 H 4.9 Cl 13.2 O 23.8. Found: C 58.2 H 4.9 Cl 13.1 O 24.1.

EXAMPLE 67

2-(2-Aminothiazol-4-yl)-3-(4-hydroxyphenyl)-propenoic acid ethyl ester hydrochloride (E-isomer)

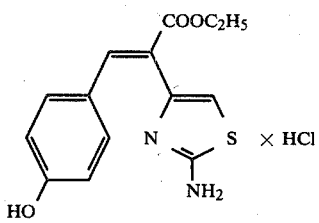

83.2 g of the product from Example 66 and 23.6 g of thiourea, dissolved in 500 ml of ethanol, were boiled under reflux for 5 hours. The mixture was evaporated, the residue was mixed thoroughly with a mixture of 200 ml of ethyl acetate and 30 ml of water and the mixture was filtered. Recrystallization of the residue from methanol gave 32 g of the pure E-isomer as the hydrochloride. Melting point: 195° to 197° (decomposition). The solution in ethyl acetate/water was adjusted to pH 8 with 2 N sodium hydroxide solution, the ethyl acetate phase was separated off and the aqueous solution was extracted twice more with ethyl acetate. Drying and evaporation of the organic phase gave an oil from which 8.2 g of the E-isomer could be crystallized as the free base by means of ethanol. An impure E/Z mixture remained as the mother liquor in the form of an oil.

IR (Nujol): 1695, 1620, 1590, 1505, 1310, 1270, 1250, 1200, 1160, 1130, 1035 cm$^{-1}$.

NMR (DMSO): $\delta$ = 7.93 [1] s, 7.27 [2] d, J = 8 Hz, 6.93 [2] d, J = 8 Hz, 6.86 [1] s, 4.26 [2] q, J = 7 Hz, 1.26 [3] t, J = 7 Hz ppm.

EXAMPLE 68

2-(2-Aminothiazol-4-yl)-3-(4-hydroxyphenyl)-propenoic acid (Z-isomer)

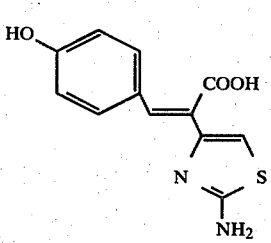

120 ml of 2 N sodium hydroxide solution were added to a solution of 21 g of the product from Example 67 in 300 ml of dioxane and the mixture was warmed to 50° to 60° for 5 hours and then left to stand at room temperature for 3 days. Working up as described in Example 26 gave 13 g of product. Melting point: 178° (decomposition).

IR (Nujol): 1630, 1580, 1510, 1420, 1335, 1305, 1280, 1240, 1170 cm$^{-1}$.

NMR (DMF): $\delta$ = 7.39 [2] d, J = 8 Hz, 7.07 [1] s, 6.78 [2] d, J = 8 Hz, 6.45 [1] s ppm.

EXAMPLE 69

2-(5-Methylisoxazol-3-ylidene)-3-oxo-4-chlorobutyric acid ethyl ester

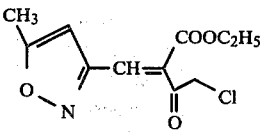

79.5 g of 5-methylisoxazole-3-aldehyde were reacted with 4-chloroacetoacetic acid ethyl ester as described in Example 24. A crude product, which was chromatographically pure, was obtained. This isomer ratio was 2:1.

IR (film): 2950, 1720, 1590, 1420, 1255, 1225, 1020 cm$^{-1}$.

NMR (CDCl$_3$): $\delta$ = 7.64/7.61 [1] s, 6.21/6.08 [1] s, 4.47 [2] s, 4.40/4.32 [2] q, J = 7 Hz, 2.43 [3] s, 1.32 [3] t, J = 7 Hz ppm.

EXAMPLE 70

2-(2-Aminothiazol-4-yl)-3-(5-methylisoxazol-3-yl)-propenoic acid ethyl ester

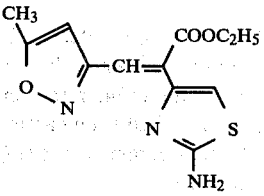

79.5 g of the product from Example 69 were reacted as described in Example 25. The crude product was purified by chromatography on silica gel (mobile phase: methylene chloride/methanol 95:5). 74.5 g of the isomer mixture were obtained.

Isomer A

IR (Nujol): 3350, 3250, 3100, 1700, 1625, 1590, 1540, 1250, 1210, 1160, 1040, 1020 cm$^{-1}$.

NMR (DMSO): $\delta$ = 7.25 [2] s broad, 7.20 [1] s, 6.70 [1] s, 6.21 [1] s, 4.38 [2] q, J = 7 Hz, 2.41 [3] s, 1.25 [3] t, J = 7 Hz ppm.

EXAMPLE 71

2-(2-Aminothiazol-4-yl)-3-(5-methylisoxazol-3-yl)-propenoic acid (Z-isomer)

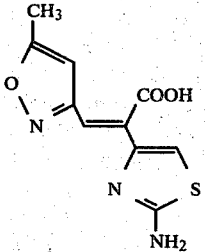

50 g of the isomer mixture prepared according to Example 70 were dissolved in 200 ml of ethanol. The solution was adjusted to pH 13.5 by the addition of 2 N sodium hydroxide solution and was left to stand at pH 13.5 and at room temperature for 24 hours. The ethanol was then stripped off, 100 ml of water were added, the pH was adjusted to 8 and the mixture was extracted three times with ethyl acetate. Evaporation of the organic phase gave 20 g of crude product, which were dissolved in a mixture of 70 ml of dioxane and 70 ml of 2 N sodium hydroxide solution. The solution was boiled under reflux for 5 hours and was then worked up according to Example 31, and the crude product was recrystallized from acetone/methanol 1:3 Yield: 7 g, melting point: 180° to 182° (decomposition).

IR (Nujol): 1600, 1460, 1400, 1290 cm$^{-1}$.

NMR (DMSO): δ=7.02 [1] s, 6.63 [1] s, 6.26 [1] s, 2.41 [3] s, ppm.

EXAMPLE 72

2-Naphthylidene-3-oxo-4-chlorobutyric acid ethyl ester

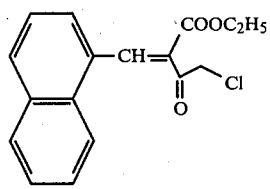

9.85 g of 1-naphthaldehyde were reacted with 15.2 g of 4-chloroacetoacetic acid ethyl ester in the course of 10 hours as described in Example 24. After incipient distillation under a high vacuum had been carried out, a 2:1 isomer mixture which still contained traces of aldehyde remained as the residue.

NMR (CDCl$_3$): δ=8.12/8.06 [1] s, 7.33–8.0 [7] m, 7.26/7.20 [1] s, 4.55/4.05 [2] s, 4.39/4.10 [2] c, J=7 Hz, 1.33/0.90 [3] t, J=7 Hz ppm.

EXAMPLE 73

2-(2-Aminothiazol-4-yl)-3-naphthylpropenoic acid ethyl ester

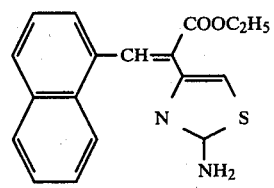

18 g of the crude product prepared as described in Example 72 were stirred with 4.6 g of thiourea in 100 ml of ethanol at 50° for 3 hours. Working up as described in Example 44 gave a crude product, from which 6.3 g of the E-isomer of melting point 155° to 157° could be crystallized with ether. An E/Z mixture remained in the mother liquor.

E-isomer

NMR (DMSO): δ=8.18 [1] s, 7.1–8.1 [7] m, 6.85 [2] s broadened, 6.20 [1] s, 4.26 [2] q, J=7 Hz, 1.28 [3] t, J=7 Hz ppm.

Z-isomer

NMR (DMSO): δ=8.06 [1] s, 7.1–8.1 [7] m, 7.26 [2] s broadened, 6.70 [1] s, 4.08 [2] q, J=7 Hz, 0.9- [3] t, J=7 Hz ppm.

EXAMPLE 74

7-[2-(2-Aminothiazol-4yl)-2-(2,3,6-trichlorbenzylidene)acetamido]-3-(1-methyl-1-H-tetrazol-5-yl)thiomethyl-3-cephem-4-carboxylic acid (Z-isomer)

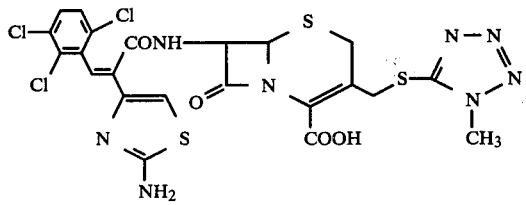

0.7 g of 7-Amino-3-(1-methyl-1-H-tetrazol-5-yl)thiomethyl-3-cephem-4-carboxylic acid were dissolved in 40 ml of 50 percent strength aqueous tetrahydrofuran at pH 7 to 8 with triethylamine 1 g of the product from Example 53 was introduced at 0°, during which the pH was kept at 7.5 by addition of triethylamine. The mixture was subsequently stirred at room temperature for 3 hours and the tetrahydrofuran was then stripped off. The aqueous solution was adjusted to pH 3.0 and the resulting suspension was then stirred at 50° for 3 hours. After decanting from an eventually formed oily residue the aqueous suspension was adjusted to pH 2.8 and the product was filtered off and dried. Yield 0.4 g.

IR (KBr): 1785, 1630, 1517, 1436, 1385, 1235, 1178 cm$^{-1}$.

NMR (CD$_3$OD): δ=7.52[1]d, J=8 Hz, 7.42[1]d, J=8 Hz, 7.16[1]s, 7.10[1]s, 5.69[1]d, J=5 Hz, 5.03[1]d, J=5 Hz, 4.31[2]s breit, 4.01[3]s, 3.78[1]d, J=18 Hz, 3.65[1]d, J=18 Hz ppm.

EXAMPLE 75

Sodium-7-[2-(-2-aminothiazol-4-yl)-2-(2,6-dichlorobenzylidene)acetamido]-3-(1-methyl-1-H-tetrazol-5-yl)thiomethyl-3-cephem-4-carboxylate (Z-isomer))

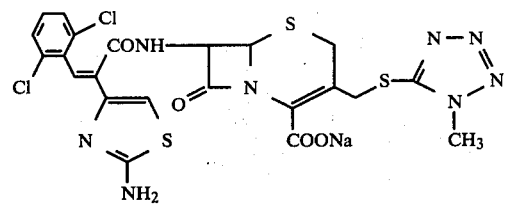

2 g of the product from Example 54 were reacted with 1.8 g of 7-amino-3-(1-methyl-1-H-tetrazol-5-yl)thiomethyl-3-cephem-4-carboxylic acid as described in Example 38. 1.6 g of the sodium salt were obtained.

IR (Nujol): 1750, 1595 cm$^{-1}$.

NMR (CD$_3$OD): δ=7.34[1]s, 7.27[3]m, 6.73[1]s, 5.62[1]d, J=5 Hz, 4.95[1]d, J=5 Hz, 4.39[1]d, J=13 Hz, 4.29[1]d, J=13 Hz, 3.97[3]s, 3.66[1]d, J=18 Hz, 3.42[1]d, J=18 Hz ppm.

EXAMPLE 76

2-(2-Aminothiazol-4-yl)-3-naphthylpropenoic acid (Z-isomer)

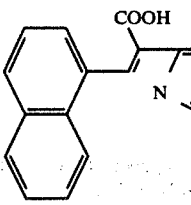

10 g of the isomer mixture prepared according to Example 73 were dissolved in 50 ml of ethanol. The solution was adjusted to pH 13.5 by the addition of 2 N sodium hydroxide solution and was stirred at room temperature for 10 hours. The ethanol was stripped off, water was added, the pH was adjusted to 8.0 and the mixture was extracted three times with ethyl acetate. The combined organic phases were washed with water and evaporated. The residue was dissolved in a mixture of 100 ml of dioxane and 30 ml of conc. sodium hydroxide solution and the solution was then boiled under reflux for 15 hours. Work-up according to Example 71 gave 2.5 g of the pure Z-isomer, melting point 220°.

IR (Nujol): 1620, 1595, 1560, 1420, 1300, 1208 cm$^{-1}$.

NMR (DMSO): δ=7.40–8.18[8]m, 7.17[2]s briet, 6.62[1]s ppm.

EXAMPLE 77

Sodium-7-[2-(2-aminothiazol-4-yl)-2-naphthylideneacetamido]penam-4-carboxylate (Z-isomer)

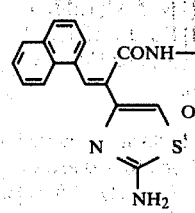

To a suspension of 0,8 g of the product from Example 76 in 20 ml of absolute methylene chloride were added 24 μl of water and 1,1 g of phosphorous pentachloride. The mixture was stirred at room temperature for 2½ hours and then the product was filtered off and washed with methylene chloride. The residue was introduced into a solution of 310 mg of 6-aminopenicillanic acid and 600 μl of triethylamine in 60 ml of methylene chloride at 0°. After stirring at 0° for 30 minutes and then at room temperature for 3½ hours the mixture was worked up according to the procedure described in Example 38.

Yield: 0.8 g of the sodium salt.

IR (Nujol): 1755, 1600 cm$^{-1}$.

NMR (CD$_3$OD): δ=8.04[1]m, 7.88[1]s, 7.68–7.80[2]m, 7.26–7.54[4]m, 6.53[1]s, 5.34[1]d, J=5 Hz, 5.28[1]d, J=5 Hz, 3.91[1]s, 1.32[3]s, 1.22[3]s ppm.

EXAMPLE 78

Sodium-7-[2-(2-aminothiazol-4-yl)-2-naphthylideneacetamido]-3-acetoxymethyl-3-cephem-4-carboxylate (Z-isomer)

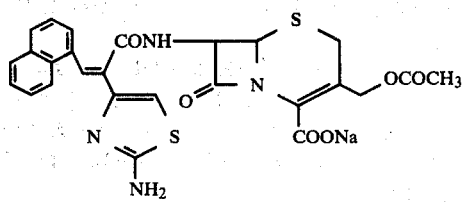

1 g of the product from Example 76 were reacted as described in Example 29, 2.6 g of the sodium salt were obtained.

IR (Nujol): 1745, 1600 cm$^{-1}$.

NMR (CD$_3$OD): δ=8.20[1]m, 8.06[1]s, 7.38–7.95[6]m, 6.66[1]s, 5.74[1]d, J=5 Hz, 4.99[1]d, J=5 Hz, 4.97[1]d, J=13 Hz, 4.78[1]d, J=13 Hz, 3.46[1]d, J=17 Hz, 3.11[1]d, J=17 Hz, 2.01[3]s ppm.

EXAMPLE 79

Sodium-7-[2-(2-aminothiazol-4-yl)-2-(5-methylisoxazol-3-ylidene)acetamido]-3-acetoxymethyl-3-cephem-4-carboxylate (Z-isomer)

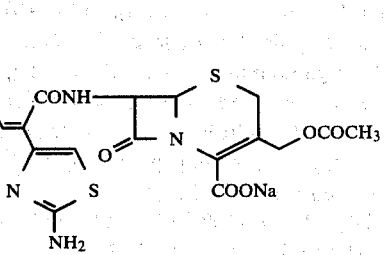

1 g of the product from Example 71 were reacted as described in Example 29. 1,5 g of the sodium salt were obtained.

IR (Nujol): 1755, 1600, 1520, 1230 cm$^{-1}$.

NMR (CD$_3$OD): δ=7.21[1]s, 6.70[1]s, 6.30[1]s, 5.91[1]d, J=5 Hz, 5.16[1]d, J=5 Hz, 5.00[1]d, J=12 Hz, 4.81[1]d, J=12 Hz, 3.61[1]d, J=18 Hz, 3.34[1]d, J=18 Hz, 2.41[3]s, 2.03[3]s ppm.

EXAMPLE 80

7-[2-(2-Aminothiazol-4-yl)-2-(4-hydroxybenzylidene)acetamido]-3-acetoxymethyl-3-cephem-4-carboxylate

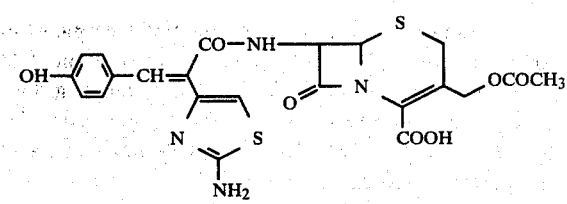

3 of the product from Example 68 were reacted as described in Example 29, 4.5 g of an EZ-isomer mixture were obtained. To a suspension of 1 g of this mixture in 25 ml of methylene chloride were added 500 μl of triethyl amine and the suspension was then stirred at room temperature over night. The product was filtered off and then suspended in 20 ml of water. After adjusting the pH to 3.0 by adding 2 N hydrochloric acid and stirring for 15 minutes the product was again filtered off and dried. Yield 0.6 g.

IR (Nujol): 1765, 1720, 1650, 1590, 1500, 1225, 1165 cm$^{-1}$.

NMR (DMSO): δ=8.56/8.15[1]d, J=8 Hz, 7.0–7.8[5]m, 6.72[1]t, J=7 Hz, 6.40/6.29[1]s, 5.84[1]m, 5.21/5.15[1]d, J=5 Hz, 5.02[1]d, J=12 Hz, 4.68[1]d, J=12 Hz, 3.66[1]d, J=17 Hz, 3.49[1]d, J=17 Hz, 2.05[3]s ppm.

EXAMPLE 81

2-Ethylidene-3-oxo-4-chlorobutyric acid ethyl ester.

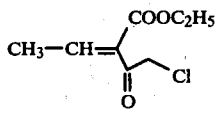

1 g of piperidine were dropped into a stirred mixture of 82 g of 4-chloroacetoacetic acid and 24 g of acetaldehyde at −20°. After stirring the mixture at −10° to −20° for 7 hours 100 ml of ethyl acetate were added and the solution was subsequently extracted three times with ice-cold 1 n hydrochloric acid and with water. The organic phase was dried over magnesium sulphate and concentrated. The oil which remained was subjected to Kugelrohr-distillation under a high vacuum.

Yield: 37 g, boiling point $_{0.05}$: 110° C. The product obtained was a Z/E mixture.

IR(CHCl$_3$): 1700, 1620, 1445, 1375, 1260 cm$^{-1}$

NRM(CDCl$_3$): δ=7.30/7.20[1]g, J=8 Hz, 4.45/4.43[1]s, 4.36/4.30[2]g, J=7 Hz, 2.10/1.95[3]d, J=8 Hz, 1.35/1.30[3]t, J=7 Hz. ppm.

EXAMPLE 82

1-(2-Aminothiazol-4-yl)-1-propencarboxylic acid ethyl ester

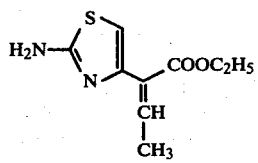

to a solution of 190 g of the product of example 81 in 400 ml tetrahydrofuran were added first a solution of 82 g sodium acetate in 150 ml of water and then 76 g thiourea. The solution was stirred at room temperature for 20 hours, then the THF was distilled off and acetic acid ethyl ester was added to the residue.

After separating off the water the organic phase was washed 2× with water. 1× with 1 m citric acid solution and 1× with water, dried and the solvent was evaporated to dry. The product was purified by chromatography an silica gel (eluent methylen chloride). Yield 10.3 g.

EXAMPLE 83

1-(2-Aminothiazol-4-yl)-1-propencarboxylic acid

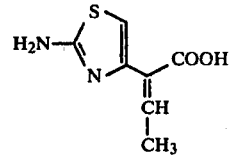

The product of example 82 was dissolved in a mixture of 20 ml methanol and 5 ml 2 n NaOH.

The solution was refluxed for 6 hours and worked up according to example 15. Yield: 2.2 g.

E-Isomer:
NMR (DMSO): δ=7.04[2]s broad, 6.89[1]q, J=7 Hz, 6.48[1]s, 1.88[6]d, J=7 Hz ppm.

Z-Isomer:
NMR (DMSO): δ=6.54[1]q, J=7 Hz, 6.48[1]s, 1.81[6]d, J=7 Hz ppm.

EXAMPLE 84

7-[1-(2-Aminothiazol-4-yl)-1-propencarbamido]-3-acetoxymethyl-3-cephem-4-carboxylic acid

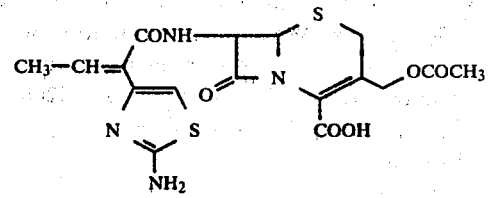

Z-Isomer 1 g of the Z-isomer of example 83 was reacted analogously to Example 19. 0.6 g of product were obtained.

NMR (DMSO): δ=9.39[1]d, J=7 Hz, 7.10[2]s, broad, 6.33[1]q, J=7 Hz, 6.24[1]s, 5.82[1]dd, J=4 Hz, J=7 Hz, 5.20[1]d, J=4 Hz, 5.01[1]d, J=13 Hz, 4.71[1]d, J=13 Hz, 5.66[1]d, J=18 Hz, 3.52[1]d, J=18 Hz, 2.06[3]s, 1.84[6]d, J=7 Hz ppm.

E-isomer 1 g of the E-isomer of example 83 was reacted analogously to Example 19. 0.6 g of product were obtained.

NMR (DMSO): δ=9.20[1]d, J=9 Hz, 7.90[2]s, very broad, 6.87[1]q, J=7 Hz, 6.64[1]s, 5.81[1]dd, J=9 Hz, J=5 Hz, 5.15[1]d, J=5 Hz, 5.02[1]d, J=13 Hz, 4.67[1]d, J=13 Hz, 3.65[1]d, J=18 Hz, 3.50[1]d, J=18 Hz, 2.03[3]s, 1.90[6]d, J=7 Hz ppm.

In analogy to example 84 was obtained:
7-[1-(2-Aminothiazol-4-yl)-1-butencarbamido]-3-acetoxymethyl-3-cefem-4-carboxylic acid.

Z-isomer
NMR (DMSO) δ=9.25[1]d, J=7 Hz, 7.00[2]s, broad, 6.23[1]t, J=7 Hz, 6.19[1]s, 5.79[1]dd, J=7 Hz, J=6 Hz, 5.17[1]d, J=6 Hz, 4.98[1]d, J=12 Hz, 4.67[1]d, J=12 Hz, 3.62[1]d, J=18 Hz, 3.50[1]d, J=18 Hz, 2.18[2]dq, J=7 Hz, J=7 Hz, 2.04[3]s, 1.01[3]t, J=7 Hz ppm.

E-isomer
NMR (DMSO) δ=9.08[1]d, J=8 Hz, 8.0[2]s very broad, 6.77[1]t, J=7 Hz, 6.63[1]s, 5.80[1]dd, J=8 Hz, J=5 Hz, 5.15[1]d, J=5 Hz, 5.01[1]d, J=13 Hz, 4.69[1]d, J=13 Hz, 3.66[1]d, J=18 Hz, 3.49[1]d, J=18 Hz, 2.29[2]dq, J=7 Hz, J=7 Hz, 2.05[3]s, 1.02[3]t, J=7 Hz ppm.

Similarly there were obtained:

7-[1-(2-Aminothiazol-4-yl)-1-undecencarbamido]-3-acetoxymethyl-3-cephem-4-carboxylic acid 7-[1-(2-Aminothiazol-4-yl)-3,3-dimethyl-1-butencarbamido]-3-acetoxymethyl-3-cephem-4-carboxylic acid 7-[1-(2-Aminothiazol-4-yl)-3-methyl-1-butencarbamido]-3-acetoxy-methyl-3-cephem-4-carboxylic acid 7-[1-(2-Aminothiazol-4-yl)-2-cyclohexyl-1-ethancarbamido]-3-acetoxymethyl-3-cephem-4-carboxylic acid 7-[1-(2-Aminothiazol-4-yl)-2-cyclopentyl-1-ethylencarbamido]-3-acetoxymethyl-3-cephem-4-carboxylic acid 7-[1-(2-Aminothiazol-4-yl)-2-cycloheptyl-1-carbamido]-3-acetoxymethyl-3-cephem-4-carboxylic acid 7-[1-(2-Aminothiazol-4-yl)-3-methoxy-1-propencarbamido]-3-acetoxymethyl-3-cephem-4-carboxylic acid 7-[1-(2-Aminothiazol-4-yl)-3-ethoxy-1-propencarbamido]-3-acetoxymethyl-3-cephem-4-carboxylic acid 7-[1-(2-Aminothiazol-4-yl)-4-dimethylamino-3,3-dimethyl-1-butencarbamido]-3-acetoxymethyl-3-cephem-4-carboxylic acid 7-[1-(2-Aminothiazol-4-yl)-3-dimethylaminomethyl-3-methyl-1-hexencarbamido]-3-acetoxymethyl-3-cephem-4-carboxylic acid 6-[1-(2-Aminothiazol-4-yl)-3,3-dimethyl-1-butencarbamido]-penam-carboxylic acid 7-[1-(2-Aminothiazol-4-yl)-3,3-dimethyl-1-butencarbamido]-3-(1-methyl-1-H-tetrazol-5-yl)thiomethyl-3-cephem-4-carboxylic acid 6-[1-(2-Aminothiazol-4-yl)-1-propencarbamido]-penam-carboxylic acid 7-[1-(2-Aminothiazol-4-yl)-1-propencarbamido]-3-(1-methyl-1-H-tetrazol-5-yl)thiomethyl-3-cephem-4-carboxylic acid 7-[1-(2-Aminothiazol-4-yl)-4-dimethylamino-3,3-dimethyl-1-butencarbamido]-3-(1-methyl-1-H-tetrazol-5-yl)thiomethyl-3-cephem-4-carboxylic acid 6-[-1-(2-Aminothiazol-4-yl)-4-dimethylamino-3,3-dimethyl-1-butencarbamido]-penam-carboxylic acid 6-[1-(2-Aminothiazol-4-yl)-3-methoxy-1-propencarbamido]-penam-carboxylic acid 7-[1-(2-Aminothiazol-4-yl)-3-methoxy-1-propencarbamido]-3-(1-methyl-1-H-tetrazol-5-yl)thiomethyl-3-cephem-4-carboxylic acid 7-[1-(2-Aminothiazol-4-yl)-1-pentencarbamido]-3-acetoxymethyl-3-cephem-4-carboxylic acid 7-[1-(2-Aminothiazol-4-yl)-1-hexencarbamido]-3-acetoxymethyl-3-cephem-4-carboxylic acid 7-[1-(2-Aminothiazol-4-yl)-1-heptencarbamido]-3-acetoxymethyl-3-cephem-4-carboxylic acid 7-[1-(2-Aminothiazol-4-yl)-1-octencarbamido]-7-acetoxymethyl-3-cephem-4-carboxylic acid 7-[1-(2-Aminothiazol-4-yl)-1-nonencarbamido]-3-acetoxymethyl-3-cephem-4-carboxylic acid 7-[1-(2-Aminothiazol-4-yl)-1-decencarbamido]-3-acetoxymethyl-3-cephem-4-carboxylic acid It will be understood that the specification and examples are illustrative but not limitative of the present invention and that other embodiments within the spirit and scope of the invention will suggest themselves to those skilled in the art.

We claim:

1. A β-lactam compound of the formula

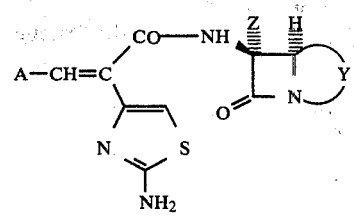

in which

A is a hydrogen atom, an alkyl, alkenyl, alkinyl or cycloalkyl group with up to 18 carbon atoms which may be substituted by double bonded oxygen, nitrogen, sulphur or by alkoxy with up to 2 carbon atoms or by dimethylamino; or naphthyl or a phenyl radical of the formula

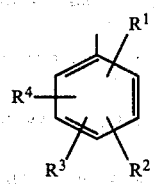

wherein $R^1$, $R^2$, $R^3$ and $R^4$ independently of one another denote a hydrogen or halogen atom, an alkyl, alkenyl, alkinyl or cycloalkyl group with up to 6 carbon atoms, a —$OCOR^5$ group,

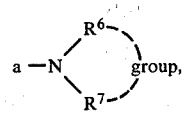

or a hydroxyl, trifluoromethyl, nitro, cyano, $C_1$ to $C_6$ alkoxy, $C_1$ to $C_6$ alkylthio, hydroxycarbonyl, ($C_1$ to $C_6$ alkoxy)-carbonyl, aminocarbonyloxy, sulphonyl or sulpho group, wherein $R^5$ denotes a branched or unbranched alkyl, alkenyl or alkinyl group with up to 6 carbon atoms and wherein $R^6$ and $R^7$ independently of one another are a hydrogen atom, or together or independently of one another denote an alkyl, alkenyl, alkinyl, cycloalkyl group or an alkanoyl group with 1–6 carbon atoms, or a heterocyclic 5-membered or 6-membered ring with 1–4 heteroatoms which may be substituted by methyl and wherein Y is

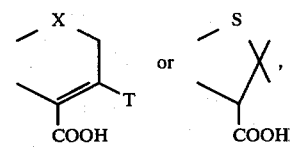

X is a sulphur or oxygen atom,

T denotes a hydrogen atom, a $C_1$ to $C_4$ alkyl group, a halogen atom or a $C_1$ to $C_4$ alkoxy, hydroxymethyl, formyloxymethyl, ($C_1$ to $C_4$ alkyl)-carbonyloxymethyl, aminocarbonyloxymethyl, pyridiniummethyl, 4-carbamoylpyridiniummethyl or heterocyclylthiomethyl group, wherein "heterocyclyl" represents a radical of the formula

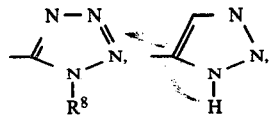

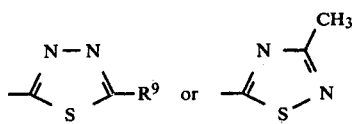

wherein $R^8$ denotes a hydrogen atom or a methyl, 2-dimethylaminoethyl, carboxymethyl, or sulphomethyl group and $R^9$ denotes a hydrogen atom or a methyl group and wherein Z denotes a hydrogen atom or a $C_1$ to $C_6$ alkoxy group, or an ester or salt thereof.

2. A compound according to claim 1, in which

Z is a hydrogen atom or a methoxy group,

X is a sulphur atom,

T is

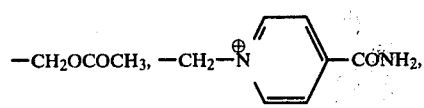

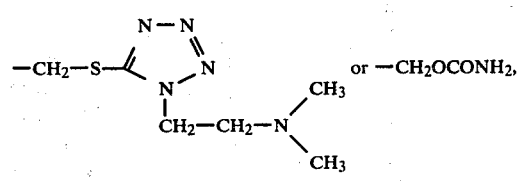

A is

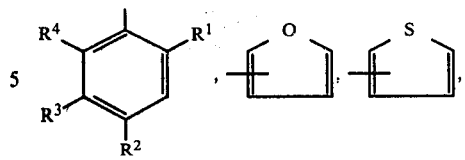

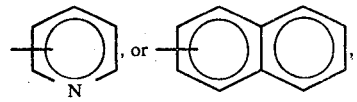

$R^6$ and $R^7$ each independently is a hydrogen atom, or together or independently of one another are alkyl, alkenyl, alkinyl or cycloalkyl group or a $C_1$ to $C_6$ alkanoyl group.

3. An antibacterial composition comprising an antibacterially effective amount of a compound according to claim 1 in admixture with a diluent.

4. A composition according to claim 3 in the form of a unit dose tablet, pill, dragee, capsule, ampule, or suppository.

5. A method of combating bacterial illnesses in human and non-human animals which comprises administering to the animals an antibacterially effective amount of a compound according to claim 1.

6. An animal feed, feed formulation or drinking water containing a growth promoting amount of a compound according to claim 1.

7. A method of promoting the growth of an animal comprising administering to such animal a growth promoting amount of a compound according to claim 1.

8. A compound of the formula

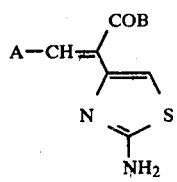

in which

A is a hydrogen atom, an alkyl, alkenyl, alkinyl or cycloalkyl group with up to 18 carbon atoms which may be substituted by double bonded oxygen, nitrogen, sulphur or by alkoxy with up to 2 carbon atoms or by dimethylamino;

B is OH, halogen or a carbonyl activating group.

* * * * *